United States Patent
Bar-Yoseph et al.

(10) Patent No.: US 9,433,599 B2
(45) Date of Patent: Sep. 6, 2016

(54) METHODS AND LIPID COMPOSITIONS FOR PROMOTING DEVELOPMENT OF GUT FLORA

(75) Inventors: Fabiana Bar-Yoseph, Haifa (IL); Yonatan Manor, Haifa (IL); Tzafra Cohen, Haifa (IL); Amit Goren, Yoqneam Illit (IL); Yael Lifshitz, Zichron Yaakov (IL)

(73) Assignee: ENZYMOTEC LTD., Migdal Haemek (IL)

( * ) Notice: Subject to any disclaimer, the term of this patent is extended or adjusted under 35 U.S.C. 154(b) by 0 days.

(21) Appl. No.: 13/643,513

(22) PCT Filed: Apr. 26, 2011

(86) PCT No.: PCT/IL2011/000330
§ 371 (c)(1),
(2), (4) Date: Oct. 25, 2012

(87) PCT Pub. No.: WO2011/135564
PCT Pub. Date: Nov. 3, 2011

(65) Prior Publication Data
US 2013/0041029 A1    Feb. 14, 2013

Related U.S. Application Data

(60) Provisional application No. 61/327,964, filed on Apr. 26, 2010.

(51) Int. Cl.
*A61K 31/23* (2006.01)
*A23L 1/29* (2006.01)
*A23L 1/30* (2006.01)

(52) U.S. Cl.
CPC ............... *A61K 31/23* (2013.01); *A23L 1/296* (2013.01); *A23L 1/3006* (2013.01)

(58) Field of Classification Search
CPC .... A61K 31/23; A61K 31/20; A61K 31/202; A61K 31/745
See application file for complete search history.

(56) References Cited

U.S. PATENT DOCUMENTS

| 5,021,245 A | 6/1991 | Borschel et al. |
| 2003/0072865 A1 | 4/2003 | Bindels et al. |

(Continued)

FOREIGN PATENT DOCUMENTS

| CN | 101437411 | 5/2009 |
| EP | 0209327 A2 | 1/1987 |

(Continued)

OTHER PUBLICATIONS

Glycerol—PubChem Compound Summary—Sep. 16, 2004.*
Kirjavainen et al ("Aberrant composition of gut microbiota of allergic infants: a target of bifidobacterial therapy at weaning?" Gut 2002;51:51-55).*
Renz-Polster et al ("Caesarean section delivery and the risk of allergic disorders in childhood" Clin Exp Allergy 2005; 35:1466-1472).*
Atopy—Meriem-Webster Online dictionary.*

(Continued)

*Primary Examiner* — Marcos Sznaidman
*Assistant Examiner* — Rayna B Rodriguez
(74) *Attorney, Agent, or Firm* — John P. White; Cooper & Dunham LLP

(57) ABSTRACT

Disclosed is a method of inducing and promoting development of beneficial gut flora in a subject and/or of reducing the frequency and duration of crying periods in a subject, the method comprises administering to the subject a lipid composition comprising a vegetable-derived fat source, wherein the fat source is a triglyceride fat source comprising triglycerides with 15-55% palmitic acid moieties out of the total fatty acids, and wherein the level of palmitic acid moieties at the sn-2 position of the glycerol backbone is at least 30% of total palmitic acid. The method is particularly intended for children. Specific fat sources, as well as food articles and a commercial package comprising the same are disclosed.

13 Claims, 1 Drawing Sheet

(56) References Cited

U.S. PATENT DOCUMENTS

| | | |
|---|---|---|
| 2003/0092590 A1 | 5/2003 | Dasque et al. |
| 2009/0131523 A1 | 5/2009 | Yosef |

FOREIGN PATENT DOCUMENTS

| | | |
|---|---|---|
| EP | 1 237 419 B1 | 9/2002 |
| WO | WO 00/56869 A2 | 9/2000 |
| WO | WO 01/41581 A1 | 6/2001 |
| WO | WO 2004/112507 A1 | 12/2004 |
| WO | WO 2004/112509 A2 | 12/2004 |
| WO | WO 2005/036987 A1 | 4/2005 |
| WO | WO 2005/051091 A1 | 6/2005 |
| WO | WO 2006/019300 A2 | 2/2006 |
| WO | WO 2006/108824 A1 | 10/2006 |
| WO | WO 2006/114791 A1 | 11/2006 |
| WO | WO 2008/005032 A1 | 1/2008 |
| WO | WO 2008/005862 A2 | 1/2008 |
| WO | WO 2009/016632 A1 | 2/2009 |
| WO | WO 2009/047754 A2 | 4/2009 |
| WO | WO 2010/003790 A1 | 1/2010 |

OTHER PUBLICATIONS

Penders et al ("Factors influencing the composition of the intestinal microbiota in early infancy." Pediatrics, 2006; 118(2):511-521.*
Hooper (Trends in Microbiology, 2004; 12(3):129-134).*
Schmelzle, H. et al. (2003). Randomized double-blind study of the nutritional efficacy and bifidogenicity of a new infant formula containing partially hydrolyzed protein, a high β—palmitic acid level, and nondigestible oligosaccharides. *Journal of Pediatric Gastroenterology and Nutrition*, 36, 343-351.
Cummings, J. H. et al. (2004). PASSCLAIM—Gut health and immunity. *Eur J Nutr*, 43(Suppl 2), II/118-II/173.
Grölund, M. M. et al. (Jan. 1999). Fecal microflora in healthy infants born by different methods of delivery: permanent changes in intestinal flora after cesarean delivery. *J Pediatr Gastroenterol Nutr.*, 28(1), 19-25.
Guarner, F. & Malagelada, J. R. (2003). Gut flora in health and disease. *The Lancet*, 360, 512-19.
Haarman, M. & Knol, J. (2006). Quantitative real-time PCR analysis of fecal *Lactobacillus* species in infants receiving a prebiotic infant formula. *Appl Environ Microbiol*, 72(4), 2359-65.
Jensen, R. G. (1999). Lipids in human milk. *Lipids*, 34(12), 1243-71.
Kallio, H. & Rua, P. (1994). Distribution of the major fatty acids of human milk between sn-2 and sn-1,3 positions of triacylglycerols. *Journal of the American Oil Chemists' Society*, 71(9), 985-992.
Kennedy, K. et al. (1999). Double-blind, randomized trial of a synthetic triacylglycerol in formula-fed term infants: effects on stool biochemistry, stool characteristics, and bone mineralization. *Am J Clin Nutr*, 70, 920-7.
Lucas, A. et al. (1997). Randomised controlled trial of a synthetic triglyceride milk formula for preterm infants. *Arch Dis Child*, 77, F178-F184.
Morais, M. B. & Jacob, C. M. (2006). The role of probiotics and prebiotics in pediatric practice. *J Pediatr (Rio J)*, 82(5 Suppl), S189-97.
Orrhage, K. & Nord, C. E. (1999). Factors controlling the bacterial colonization of the intestine in breastfed infants. *Acta Paediatr Suppl*, 88(430), 47-57.
Ouwehand, A. et al. (2002). The role of the intestinal microflora for the development of the immune system in early childhood. *Eur J Nutr*, 41(Suppl 1), I/32-I/37.
Parracho, H. et al. (2007). Probiotics and prebiotics in infant nutrition. *Proc Nutr Soc*, 66(3), 405-411.
Salminen, S. et al. (2004). Influence of mode of delivery on gut microbiota composition in seven year old children. *Gut*, 53, 1388-9.
Spurgeon, M. J. et al. (2003). An investigation of the general, reproductive and postnatal developmental toxicity of Betapol™, a human milk fat equivalent. *Food and Chemical Toxicology*, 41, 1355-1366.
Carnielli, V. P. et al. (1996). Structural position and amount of palmitic acid in infant formulas: effects on fat, fatty acid, and mineral balance. *J Pediatr Gastroenterol Nutr*, 23(5), 553-60. XP-002315050, BIOSIS Database Accession No. PREV199799383168.
Yoshioka, H. et al. (1983). Development and differences of intestinal flora in the neonatal period in breast-fed and bottle-fed infants. *Pediatrics*, 72(3): 317-21.
International Search Report, mailed Oct. 13, 2011 in connection with PCT International Application No. PCT/IL2011/000330, filed Apr. 26, 2011.
Written Opinion of the International Searching Authority, mailed Oct. 13, 2011 in connection with PCT International Application No. PCT/IL2011/000330, filed Apr. 26, 2011.
Written Opinion of the International Preliminary Examining Authority, mailed Jun. 1, 2012 in connection with PCT International Application No. PCT/IL2011/000330, filed Apr. 26, 2011.
Notification of Transmittal of the International Preliminary Report on Patentability, including International Preliminary Report on Patentability, mailed Jul. 16, 2012 in connection with PCT International Application No. PCT/IL2011/000330, filed Apr. 26, 2011.
Bourlioux, P. et al. (2003). The intestine and its microflora are partners for the protection of the host: report on the Danone Symposium "The Intelligent Intestine," held in Paris, Jun. 14, 2002. *Am J Clin Nutr*, 78(4), 675-83.
Carnielli et al., "Feeding premature newborn infants palmitic acid in amounts and stereoisomeric position similar to that of human milk: effects on fat and mineral balance" (1995) Am J Clin Nutr 1995, vol. 61, No. 5, 1037-1042.
Savino et al., "Reduction of crying episodes owing to infantile colic: a randomized controlled study on the efficacy of a new infant formula." Eur J Clin Nutr 2006; 60:1304-1310.
Laubereau et al., "Caesarean section and gastrointestinal symptoms, atopic dermatitis, and sensitization during the first year of life." Arch Dis Child 2004; 89:993-997.
Oligosaccharide, Dictionary.com, The American Heritage Stedman's Medication Dictionary, Houghton Mifflin Company, 2002.
Lievin et al., "Bifidobacterium strains from resident human gastrointestinal microflora exert antimicrobial activity", Gut (2000), 47:646-652.
Office Action issued Dec. 26, 2013 in connection with U.S. Appl. No. 13/931,590.
Final Office Action issued May 14, 2014 in connection with U.S. Appl. No. 13/931,590.
Advisory Action issued Aug. 21, 2014 in connection with U.S. Appl. No. 13/931,590.
Conly et al., "Coming full circle: From antibiotics to probiotics and prebiotics", Can. J. Infect Dis Med Microbiol, vol. 15, No. 3, pp. 161-163 (2004).
Santulli et al., "Acute Necrotizing Enterocolitis in Infancy: A Review of 64 Cases", Pediatrics, vol. 55, No. 3, pp. 372-387 (1975).
Corcoran et al., "Growth of probiotic lactobacilli in the presence of oleic acid enhances subsequent survival in gastric juice", Microbiology, 153:291-299 (2007).
Bar-Yoseph et al., "Palmitic Acid In Infant Nutrition", Palmitic Acid: Occurrence, Biochemistry and Health Effects, pp. 145-158 (2014).
Altieri et al., "Effectiveness of fatty acids and their monoglycerides against gram-negative pathogens", Int. J. Food Sci. Technol. (2009), 44:359-366.
Rigo at al., "Growth, weight gain composition and mineral accretion in term infants fed a new experimental formula containing hydrolysed protein, β-palmitate and prebiotics", Pediatrika. (2001), 21(10):387-396.
Powell at al., "Effect of Various Lipids Found in Human Milk on the Growth of Infant Bifidobacteria", J. Gen. Appl. Microbial. (1981), 27:185-193.
Cilleruelo et al., "Fórmulas adaptadas para lactantes y modificaciones actuals de éstas", An Pediatr Contin (2004), 2 (6): 325-338.

* cited by examiner

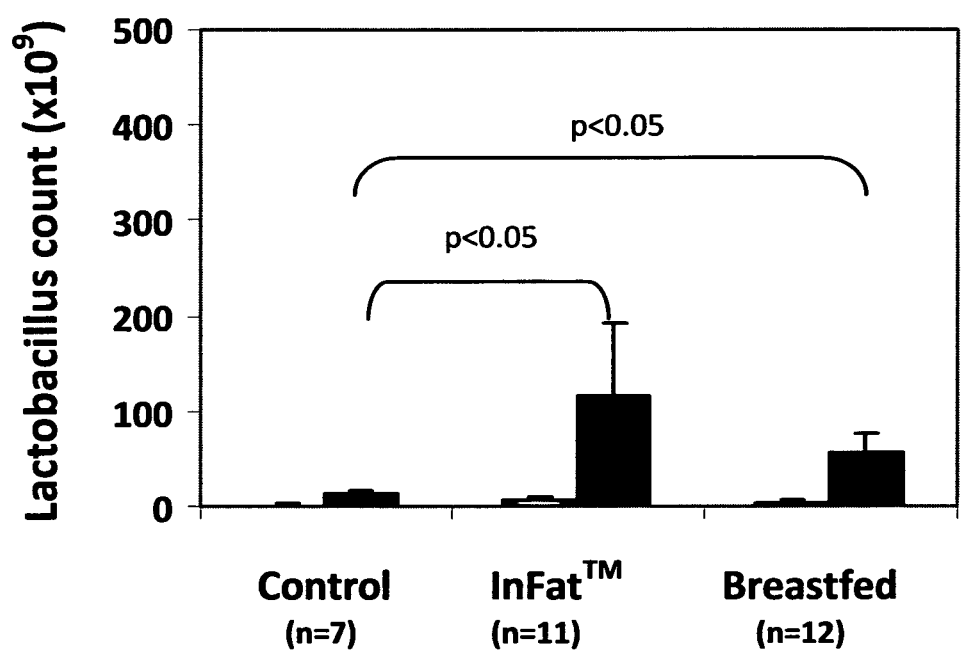

METHODS AND LIPID COMPOSITIONS FOR PROMOTING DEVELOPMENT OF GUT FLORA

CROSS-REFERENCE TO RELATED APPLICATIONS

This application is a §371 national stage of PCT International Application No. PCT/IL2011/000330, filed Apr. 26, 2011, claiming the benefit of U.S. Provisional Application No. 61/327,964, filed Apr. 26, 2010, the contents of each of which are hereby incorporated by reference in their entirety.

FIELD OF THE INVENTION

This invention relates to the field of gut flora and in particular to methods and products for enhancement of gut flora development and thereby, inter alia, enhancement of the immune system in a subject.

BACKGROUND OF THE INVENTION

As described in the art, gut flora consists of microorganisms that live in the digestive tracts of animals, and constitutes the largest reservoir of human flora. The symbiosis between the gastrointestinal tract and the large number of bacteria contributes substantially to normal digestive function. Thus, the gut flora serves as an effective bather against opportunistic and pathogenic micro-organisms, and this 'colonization resistance' is one of their most important functions.

The normal flora presents an exceedingly complex equilibrium between the microorganisms that normally reside in the gastrointestinal tract, playing an important role in nutrition, physiology, and the regulation of the host's immune system [Bourlioux, P., et al. Am J Clin Nutr 78(4): 675-83, 2003].

The numbers and species profile of gut flora varies greatly according to the region of the gastrointestinal tract, with the colon as the most heavily populated area. The majority of bacteria are nonsporing anaerobes, of which the numerically dominant are *Bacteroides* spp. and *Bifidobacterium* spp., *Eubacterium* spp., *Clostridium* spp., *Lactobacillus* spp., *Fusobacterium* spp. and various Gram-positive cocci. Bacteria present in lower numbers include *Enterococcus* spp., Enterobacteriaceae, methanogens and dissimilatory sulphate-reducing bacteria.

The importance of gut microflora is well appreciated. Flora metabolism is involved in the production of vitamins, modulation of the immune system, regulating the development of the gut, enhancement of digestion and absorption, inhibition of harmful species and removal of carcinogens and toxins and producing hormones to direct the host to store fats and in preventing the development of allergies.

Gut flora has a continuous and dynamic effect on the host's gut and the systemic immune systems. The bacteria are key components in promoting the early development of the gut's mucosal immune system in terms of both its physical components and function and continue to play a role in its operation, later in life. The bacteria stimulate the lymphoid tissue associated with the gut mucosa to produce antibodies to pathogens. The immune system recognizes and fights harmful bacteria, but does not act against the helpful/beneficiary species alone, a tolerance developed in infancy.

With respect to immunity, recent findings have shown that gut flora plays a role in the intestinal expression of Toll-like receptors (TLRs), which are a class of proteins that play a key role in the innate immune system. TLRs cause parts of the immune system to repair injury caused by radiation, for example. TLRs also provide the intestinal ability to discriminate between the pathogenic and commensal bacteria.

The human gut is sterile at birth and microbial colonization begins during delivery. The first bacteria to settle in are able to affect the immune response, making it more favorable to their own survival and less so to competing species; thus the first bacteria to colonize the gut are important in determining the person's lifelong gut flora makeup. Microflora development is then dependent on the type of feeding regime given in early life.

Breast-fed infants have a predominance of Bifidobacteria. In breastfed infants, the flora is not only much richer in bifidobacteria but also includes far fewer species liable to be pathogenic [Bourlioux et al., ibid.]. In contrast, formula-fed infants have a more complex flora which resembles that of an adult, in that *Bacteroides, Clostridia*, Bifidobacteria, Lactobacilli, Gram positive cocci, coliforms and other species are all represented in fairly equal proportions [Yoshioka, H., et al. Pediatrics 72(3): 317-21, 1983]. However, at the time of weaning there is a shift from predominantly facultative aerobic species such as Streptococci and *Escherichia coli* to mostly obligate anaerobic species. An age-related effect can be observed. The composition of the flora evolves over time, depending on the diet that the infants receive, until it resembles the flora of adults, at around 2 years of age, when it is thought to become fairly stable [Cummings, J. et al. Eur J Nutr 43 Suppl 2: II118-II173, 2004].

The gastrointestinal tract of newborns is sterile, but it becomes colonized immediately after birth with organisms from the environment, mainly from the mother. During vaginal delivery, the contact with the vaginal and intestinal flora is an important source for the start of the infant's colonization [Orrhage K & Nord C E., Acta Paediatr. 88: Suppl (430): 47-57, 1999]. During Cesarean delivery, direct contact of the mouth of the newborn with the vaginal and intestinal microbiota is absent, and environmental bacteria play an important role for infants' intestinal colonization. Some authors have suggested that the composition of the very first human microbiota could have long lasting effects, up to months [Grönlund M M, et al. J Pediatr Gastroenterol Nutr. 28: 19-25, 1999] or even years [Salminen S, et al., Gut, 53: 1388-9, 2004]. The composition of enteric microbiota in early days of life seems therefore to be a very important factor for achieving and maintaining good health in the years to come.

Thus, there is a continuous and growing need for the development of infant formulations that are can mimic the protective effects of human milk, providing for gut microflora composition as much as possible similar to that of breastfed infants.

Most commonly, probiotics are provided (as dietary product) in order to affect the composition of gut flora. In addition, prebiotics may be used. While probiotics are defined according to the World Health Organization (WHO), as living organisms, which when administered in adequate amounts, confer a health benefit on the host [Morais, M. B. and Jacob, C. M., J Pediatr (Rio J) 82(5 Suppl): S189-97, 2006], prebiotics are non-digestible food ingredients that beneficially affect the host by selectively stimulating the growth of one or limited number of bacterial species already resident in the colon having a potential to improve health [Parracho, H., et al. Proc Nutr Soc 66(3): 405-11, 2007]. As such, any dietary component that reaches the colon intact is a potential prebiotic [Cummings et al., ibid.]. A prebioticlike effect occurs when there is an increase in the activity of healthy bacteria in the human intestine. The prebiotics stimulate the growth of healthy bacteria such as bifidobacteria and lactobacilli in the gut and increase resistance to invading pathogens. Most interest in the development of prebiotics is aimed at non-digestible oligosaccharides such as fructooligosaccharides (FOS), trans-galactosylated oligosaccharide (TOS), Isomalto-oligosaccharide (IMO), xylooligosaccharides (XOS), soyoligosaccharides (SOS), galactooligosaccharides (GOS) and lactosucrose [Cummings et al., ibid.].

A relatively new development in the area of flora enrichment lies in the field of synbiotics. The term synbiotics includes incorporation of a useful probiotic into an appropriate dietary vehicle with a suitable prebiotic [Cummings et al., ibid.].

Several patent applications describe infant formulations, many of which are based on compositions combining source of proteins, source of carbohydrates, source of lipids as well as vitamins or minerals combined with source of microorganism (probiotic) and/or of prebiotic.

WO 2010/003790 describes a nutritional composition comprising free amino acids, carbohydrate source and a lipid source and can be peptide-free or protein-free. The lipid source comprises triacylglycerides enriched with palmitic acid residue at the sn-2 position of the glycerol backbone. The composition is used for treatment of allergic infants or infants with impaired intestinal absorption, for treating, preventing or alleviating such symptoms while improving calcium absorption in the intestinal tract and/or improving the fat absorption in the intestinal tract and/or softening the stool consistency.

WO 2001/41581 (EP 1 237 419) describes an infant formula comprising combinations of at least one protein component, at least one prebiotic component, at least one lipid component comprising triglycerides in which palmitic acid residues make up more than 10% (w/w) of all fatty acid residues present in the triglycerides and at least 30% of the palmitic acid residues are bonded at the sn-2 position of the triglycerol backbone.

WO 2006/019300 describes an infant nutritional composition of protein, fat, carbohydrate, nucleotide component and a negatively charged non-protein component, which mimics the protective effects of human milk particularly against allergies and infections.

WO 2008/005862 and WO2008/005032 describe infant formula comprising of fat, protein, carbohydrate, vitamins and minerals as well as on an as-fed basis: gangliosides, phospholipids, lactoferrin and sialic acid. This formulation is intended for reducing the risk of diarrhea infants, as well as producing gut microflora profile similar to that of breast-fed infants.

WO 2004/112507 describes a formula intended for both infants and young children, comprising a source of proteins, a source of carbohydrates, a source of lipids including at least one long chain polyunsaturated fatty acids (LC-PUFA) and probiotics. The formula is used for strengthening natural immune system defects and promoting a healthy mental development.

WO 2004/112509 describes a nutritional composition comprising of specific fats or non-digestible oligosaccharides and at least one microorganism for inducing a pattern of gut barrier maturation similar to that observed with breast-feeding and for further improving gut barrier maturation, ensuring an optimal barrier function in infants and/or maintaining gut barrier homeostasis.

WO2006/108824 describes an infant formula comprising a source of protein, a source of lipids, a source of carbohydrates and a probiotic. The formula is used to modulate the immune system of a neonatal infant to promote the development in the first few weeks of the life of an infant of a beneficial intestinal microbiota comparable to that found in breastfed babies as well as to promote the maturation of the immune system of a neonatal infant in the first few weeks of life.

SUMMARY OF THE INVENTION

The present invention provides, in accordance with a first of its aspects, a method of promoting development of gut flora in a subject, specifically beneficial gut flora, comprising administering to the subject an edible lipid composition comprising a vegetable-derived fat source, wherein the fat source comprises triglycerides with 15-55% palmitic acid moieties out of the total fatty acids, and wherein the level of palmitic acid moieties at the sn-2 position of the glycerol backbone is at least 30% of total palmitic acid.

In a further aspect, the present invention provides for the use of an edible lipid composition comprising a vegetable-derived fat source, wherein the fat source is a triglyceride fat source comprising triglycerides with 15-55% palmitic acid moieties out of the total fatty acids, and wherein the level of palmitic acid moieties at the sn-2 position of the glycerol backbone is at least 30% of total palmitic acid, for promoting development of gut flora in a subject, or for use in preparing a formulation for promoting development of gut flora in a subject, specifically beneficial gut flora.

In yet a further aspect, the present invention provides an edible vegetable-derived fat source for use in promoting development of gut flora in a subject, specifically beneficial gut flora, wherein the fat source is a triglyceride fat source comprising triglycerides with 15-55% palmitic acid moieties out of the total fatty acids, and wherein the level of palmitic acid moieties at the sn-2 position of the glycerol backbone is at least 30% of total palmitic acid.

In another aspect, the present invention provides a method of reducing the frequency and duration of crying periods in a subject, particularly an infant, comprising administering to the subject a lipid composition comprising a vegetable-derived fat source, wherein the fat source is a triglyceride fat source comprising triglycerides with 15-55% palmitic acid moieties out of the total fatty acids, and wherein the level of palmitic acid moieties at the sn-2 position of the glycerol backbone is at least 30% of total palmitic acid.

In a further aspect, the present invention provides for the use of an edible lipid composition comprising a vegetable-derived fat source, wherein the fat source is a triglyceride fat source comprising triglycerides with 15-55% palmitic acid moieties out of the total fatty acids, and wherein the level of palmitic acid moieties at the sn-2 position of the glycerol backbone is at least 30% of total palmitic acid, for reducing the frequency and duration of crying periods in a subject, or for use in preparing a formulation for reducing the frequency and duration of crying periods in a subject.

In yet a further aspect, the present invention provides an edible vegetable-derived fat source for use in reducing the frequency and duration of crying periods in a subject, wherein the fat source is a triglyceride fat source comprising triglycerides with 15-55% palmitic acid moieties out of the total fatty acids, and wherein the level of palmitic acid moieties at the sn-2 position of the glycerol backbone is at least 30% of total palmitic acid.

In another aspect, the present invention provides a food article, wherein the food article comprises the vegetable-derived lipid composition (fat source) in accordance with the invention, as described above and below in connection with the aspects of promoting development of gut flora in a subject, specifically beneficial gut flora.

In another aspect the present invention provides a food article, wherein the food article comprises the vegetable-derived lipid composition (fat source) in accordance with the invention, as described above and below, for use in reducing the frequency and duration of crying periods in a subject, specifically an infant.

In yet a further aspect, the present invention provides a commercial package comprising:

a) an edible vegetable-derived fat source which upon enteral administration to a subject promotes development of gut flora in a subject, specifically beneficial gut flora;

b) optionally at least one of edible physiologically acceptable protein, carbohydrate, vitamin, mineral and active or non-active additives;

c) optionally at least one edible physiologically acceptable carrier or diluent for carrying the constituent/s defined in a) and b);

d) means and receptacles for admixing the constituents defined in a), b) and/or c); and e) instructions for use.

In yet a further aspect, the present invention provides a commercial package comprising:

a) an edible vegetable-derived fat source which upon enteral administration to a subject reduces the frequency and duration of crying periods in a subject, specifically an infant;

b) optionally at least one of edible physiologically acceptable protein, carbohydrate, vitamin, mineral and active or non-active additives;

c) optionally at least one edible physiologically acceptable carrier or diluent for carrying the constituent/s defined in a) and b);

d) means and receptacles for admixing the constituents defined in a), b) and/or c); and e) instructions for use.

In some embodiments, the lipid composition defined herein provides one or more of at least the following beneficial effects:

it has an effect on colonization of at least one pathogenic bacteria in the gut of the subject, the effect being selected from the group consisting of inhibiting, preventing and reducing colonization of the at least one pathogenic bacteria;

it has an effect on colonization of at least one of bifidobacteria and/or lactobacilli bacteria in the gut of the subject, the effect being selected from the group consisting of enhancing, increasing and promoting colonization of the at least one of bifidobacteria and/or lactobacilli bacteria; —it has a beneficiary effect on the immune system;

it has an effect on the development of gut flora in the gut of a subject, the effect may comprise one or more of (i) promoting development of gut flora comprising predominantly bifidobacteria and lactobacilli; (ii) increasing the abundance of bifidobacteria and lactobacilli; and (iii) reducing colonization of the at least one pathogenic bacteria;

it has an effect on pH level in the gut of the subject, wherein the effect comprises decrease of the pH level in the gut (as determined, e.g. from a stool sample from the subject); and it has an effect on the crying period of the subject e.g., infant, wherein the effect may comprise reducing the number of crying periods (spells) and/or reducing the frequency, duration and/or intensity of the infant crying.

The effect on the immune system may be, but is not limited to an effect comprising one or more of (i) treatment at least one disorder of the immune system of the subject, more specifically where the at least one disorder of the immune system may result from gut flora imbalance in the subject; (ii) strengthening of the immune system of the subject; (iii) prevention (and/or reduction of incidence) of the development of immune disorders; and (iv) improving the response of the subject to vaccination.

With regard to crying, in specific embodiments the reduction effect is not related to the subjects stool characteristics.

In some embodiments, the at least one disorder of the immune system is selected from inflammation, allergy, atopy, feeding intolerance and infection and the lipid composition is effective to treat the disorder.

It is noted that in the various aspects and embodiments of the invention the subject may be a healthy subject. In such embodiments the effect of the composition according to the invention may be preventive.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 illustrates the effect of the method according to the invention on the beneficial bacteria count in the gut flora of the tested subjects.

DETAILED DESCRIPTION OF THE INVENTION

While the invention is described in the following detailed description with reference to a method of using a lipid composition according to the invention in promoting beneficial gut flora development and/or in reducing the frequency and duration of crying periods in a subject, it is to be understood that also encompassed within the present disclosure is the use of the lipid composition of the invention for promoting beneficial gut flora development and/or for reducing the frequency and duration of crying periods in a subject as well as the remaining aspects of the invention as disclosed herein above and below.

The inventors of the instant invention have shown that infants who were fed with the lipid composition according to the invention e.g., infant formula comprising suitable structured lipid, as described herein, e.g. InFat™ as a non-limiting example, demonstrated intestinal flora profile that was similar to that of infants that were breastfed (as detailed herein below in Examples 3 and 4). Further, it was surprisingly found by the inventors that infants fed with a diet rich in palmitic acid at the sn-2 position, as in the lipid compositions employed by the present invention, experienced reduction in the number of pathogenic bacteria in the gut (as illustrated herein below in Tables 10 and 12) while the number of beneficial bacteria in the gut increased (as illustrated in FIG. 1 and in Tables 9 and 11 herein below). Furthermore, the inventors surprisingly found that infants fed with the lipid composition according to the invention showed statistically significant less crying, in intensity and duration of crying and also frequency of crying spells/periods (as illustrated for example herein below in Example 5 and in Table 13).

Thus, firstly, the present invention provides a method and a lipid composition therefor, for promoting, in a subject such gut flora which is beneficial to the subject e.g., gut flora characterized by abundance of bacteria which contribute to and/or have positive effects on the digestive function.

In one of its aspects the present invention provides a method of promoting development of beneficial gut flora in a subject, the method comprises administering to the subject a lipid composition comprising a fat source, more specifically a vegetable oil fat source, wherein the fat source is a triglyceride, more specifically vegetable-derived triglyceride fat source comprising triglycerides with about 15 to about 55% (% w/w throughout the text, unless otherwise indicated) palmitic acid moieties out of the total fatty acids, and wherein the level of palmitic acid moieties at the sn-2 position of the glycerol backbone is at least about 30% of total palmitic acid.

In another of its aspects, the present invention provides a method of reducing the frequency and duration of crying periods in a subject, e.g., an infant, comprising administering to the subject a lipid composition comprising a vegetable-derived fat source, wherein the fat source is a triglyceride fat source comprising triglycerides with 15-55% palmitic acid moieties out of the total fatty acids, and wherein the level of palmitic acid moieties at the sn-2 position of the glycerol backbone is at least 30% of total palmitic acid.

In yet another of its aspects, the present invention provides an edible fat source, more specifically vegetable-derived fat source, for use in promoting development of gut flora in a subject, wherein said fat source is a triglyceride fat source, more specifically vegetable-derived fat source, comprising triglycerides, more specifically vegetable-derived or vegetable-derived structured triglycerides with about 15 to about 55% palmitic acid moieties out of the total fatty acids, and wherein the level of palmitic acid moieties at the sn-2 position of the glycerol backbone is at least about 30% of total palmitic acid.

It is noted that as used herein, the term "palmitic acid ratio" means the level of palmitic acid moieties at the sn-2 position of the glycerol backbone as % of total palmitic acid in the triglyceride composition (oil). This "palmitic acid ratio" is also referred to herein as "ratio", and is specifically as defined and exemplified below.

In yet a further aspect, the present invention provides the use of an edible lipid composition comprising a vegetable-derived fat source, wherein the fat source is a triglyceride fat source comprising triglycerides with about 15 to about 55% palmitic acid moieties out of the total fatty acids, and wherein the level of palmitic acid moieties at the sn-2 position of the glycerol backbone is at least about 30% of total palmitic acid, for promoting development of beneficial gut flora in a subject or for preparing a formulation for promoting development of beneficial gut flora in a subject.

In the context of the invention, the term "promoting development of gut flora" is used to denote any one of enhancing, inducing, stimulating and similar effects on the construction and or generation of gut (intestine) flora in a subject. The gut flora in the context of the invention refers to bacterial gut population within at least a portion of the intestinal tract. In some embodiments the abundance of bifidobacteria and/or lactobacilli in the gut flora is increased. In some further embodiments the bacterial gut population is predominantly enriched with bifidobacteria and/or lactobacilli, meaning that bifidobacteria and/or lactobacilli are more abundant. Thus, in some embodiments the lipid composition in accordance with the invention increases the abundance of bifidobacteria and/or lactobacilli in the gut flora of the treated subject. The term "promoting development of gut flora" is also referred to herein as "promoting development of beneficial gut flora". In all embodiments and aspects of the invention the beneficial gut flora may be essentially equivalent and/or comparable to gut flora of breastfed subject.

In some embodiments the lipid composition is effective to promote development of gut flora comprising predominantly bifidobacteria and lactobacilli.

In some embodiments, the lipid composition is effective to maintain normal gut flora profile.

In yet further embodiments, the lipid composition is effective to induce the onset of gut flora thus providing an advantage e.g., when administered after birth, for example from day one, or beginning later after birth.

Further, in the context of the invention, it is to be understood that by promoting the development of gut flora, a favorable effect also may take place against colonization of pathogenic bacteria. Thus, the term "promoting development of gut flora" also denotes reducing, inhibiting and/or eliminating the colonization of pathogenic bacteria in the gut. Such pathogenic bacteria that may be affected by the presence of favorable gut flora (as compared to standard reference as discussed below) include, without being limited thereto, coliform organisms, enterobacteria, *clostridia, staphylococcus, veillonella*, proteus, *P. aeruginosa, clostridium* and different types of streptococci.

Further, the term "promoting development of gut flora" is to be understood as encompassing an effect on the gut pH level, i.e. a reduction of pH level in the gut. It is appreciated that in healthy breastfed infants the pH in the gut is typically between about 5.5 and 6.5. The pH of the gut may be determined based on stool samples obtained from the treated subject.

Yet further, the term "promoting development of gut flora" is to be understood as encompassing a beneficial effect on the immune system of subject, whereby at least one or more of the following is achieved: (i) treating at least one disorder of the immune system of the subject, the at least one disorder of the immune system being as a result of gut flora imbalance in the subject; (ii) strengthening the immune system of the subject. Gut flora imbalance may be exhibited by low level of flora as well as by an imbalance in the flora population etc. as compared to the flora of a healthy breast-fed infant. The disorder may be a chronic or acute disorder, and it may be a disorder involved with a reduced or weakened (immune deficiency) or, on the other hand, elevated function of the immune system (hyper-immune system). Such disorder may be selected from the group consisting of inflammation, atopy (e.g. allergy, asthma, eczema, rhinitis and atopic dermatitis), feeding intolerance and infection without being limited thereto. When referring to strengthening of the immune system it is to be understood as including induction, stimulation, enhancement and the like of a weaken immune system as well as of a healthy immune system.

In the context of the present invention the term "treatment" or "treating" and the like are used herein to refer to obtaining a desired pharmacological and physiological effect on the subject, including prophylactic in terms of "preventing" or partially preventing an undesired condition or symptoms from developing and/or therapeutic in terms of "curing" partial or complete curing of an already existing undesired condition. The term "treating" is used within the context of this application as treatment of subjects who are healthy and/or suffer from a disorder, disease, or impaired physiological/medical condition.

In some embodiments, the lipid composition is effective to promote beneficial gut flora development to obtain a gut flora profile that is essentially equivalent and/or comparable to pre-determined or known normal gut flora profile in a healthy breastfed infant. The normal gut flora profile is determined based on a pre-determined level from a group of healthy breastfed infants. A level that is essentially equivalent/comparable to that of a pre-determined normal profile includes deviations from the normal level of about 5%, at times, about 10% and even up to about 15% from the predetermined level.

In some embodiments the method according to the invention is utilized for developing a gut flora profile that is essentially equivalent/comparable to that of a breastfed infant.

As mentioned above, in all of the various aspects and embodiments of the invention, the fat source is derived from a vegetable source.

In the various aspects and embodiments of the invention, the lipid composition may have an effect on colonization of at least one pathogenic bacteria in the gut of the subject, wherein the effect is selected from the group consisting of inhibiting, preventing and reducing colonization of the at least one pathogenic bacteria.

In the various aspects and embodiments of the invention, the lipid composition may have a beneficiary effect on the immune system of the subject. In some embodiments, the subject suffers from at least one disorder of the immune system resulting from or associated with gut flora imbalance.

In the various aspects and embodiments of the invention, the at least one disorder in the immune system is selected from inflammation, atopy, allergy, feeding intolerance and infection and the lipid composition is effective to treat or prevent or reduce the severity of the disorder. In some embodiments the atopy is selected from the group consisting of allergy, asthma, eczema, rhinitis and atopic dermatitis.

In the various aspects and embodiments of the invention, the lipid composition may promote development of gut flora abundant with bifidobacteria and/or lactobacilli. In some embodiments the promoted gut flora comprises predominantly bifidobacteria and/or *lactobacillus*.

In the various aspects and embodiments of the invention, the lipid composition may enhance colonization (increase the abundance) of the at least one beneficial bacterium in the gut of the subject. More specifically the bacteria may be selected from the group consisting of bifidobacteria and lactobacilli.

In the various aspects and embodiments of the invention, the lipid composition may inhibit colonization of the at least one pathogenic bacteria in the gut of the subject. In some embodiments the pathogenic bacteria is selected from the group consisting of coliform organisms, enterobacteria, *clostridia, veillonella*, proteus, *P. aeruginosa, clostridium, staphylococus* and streptococci. In some embodiments the pathogenic bacteria are *clostridium* and/or *staphylococcus*.

The subject in accordance with a specific embodiment of the invention is a human child. Further, the term "child" denotes infants (from day of birth, newborn, to about 12 months i.e., about 1 year) as well as toddlers (from about one year up to about the age of 3). The infant may be pre-term infant and term infant, as well as an infant born by regular delivery, cesarean surgery (Caesarean section) as well as any other modes of delivery. The term "newborn" includes pre-mature infants, post-mature infants and full term newborns.

In some embodiments the method of the invention comprises providing the lipid composition to the infant for a period of time from day one to weeks following birth.

In some embodiments, the child is one being diagnosed (by standard techniques) of having or susceptible of developing at least one of the following:

an imbalanced level e.g. low level or an imbalance in the profile of gut flora population, particularly as compared to gut flora profile of breastfed infants;

a disorder in the immune system that is associated with imbalance in level or imbalance in the profile of gut flora population;

a disorder related or caused by a disorder of the immune system that is associated with an imbalance in the gut flora level (e.g. low flora level) or an imbalance in the profile of gut flora population. The disorder may be, without being limited thereto, inflammation, atopy (e.g. allergy, asthma, eczema, rhinitis and atopic dermatitis), feeding intolerance and infection.

Subject populations at risk for the aforementioned disorders include but are not limited to children born prematurely, infants born by Caesarean section, vegetarians, naturalistics, subjects taking medicines e.g., antibiotics which may affect their gut flora, subjects with limited or deficient nutrition, subjects subjected to cancer therapy e.g., chemotherapy and/or radiation which may affect their gut flora.

Thus, in the various aspects and embodiments of the invention, the subject may be a child. The child may be an infant or a toddler. In some embodiments the infant is one delivered by a Caesarean section. In some embodiments the infant is a newborn that may be pre-term infant and term infant. In some embodiments the subject is prone to or at risk of developing an imbalanced profile of the gut flora population compared to breastfed infants. In some embodiments the subject is at risk of developing a disorder associated with imbalance in the profile of the gut flora population compared to breastfed infants. In some embodiments the subject is at risk of developing an imbalance in the profile of the gut flora population. In some embodiments the subject is formula fed and therefore at risk of developing an imbalance in the profile of the gut flora population compared to breastfed infants.

In the various aspects and embodiments of the invention, the lipid composition may be effective in promoting beneficial gut flora development, to obtain a gut flora profile that is essentially equivalent to pre-determined or known normal gut flora profile of a healthy breastfed infant.

In all aspects of the invention and embodiments the lipid composition is effective in developing a beneficial gut flora profile that is essentially equivalent or comparable to that of a breastfed infant.

In the various aspects and embodiments of the invention, the lipid composition may be provided to the infant for a period of time from day one to weeks, months, etc. following birth.

The triglycerides according to the invention may comprise saturated and/or mono-unsaturated and/or poly-unsaturated fatty acids residues.

In the various aspects and embodiments of the invention, the fatty acid residues at the sn-2 position of the glycerol backbone may be a saturated fatty acid residue, including $C_8$ to $C_{24}$, and in some particular embodiments $C_{14}$-$C_{18}$ fatty acid residues.

The saturated fatty acid may be any one of butyric acid (butanoic acid, C4:0), caproic acid (hexanoic acid, C6:0), caprylic acid (octanoic acid, C8:0), capric acid (decanoic acid, C10:0), lauric acid (dodecanoic acid, C12:0), myristic acid (tetradecanoic acid, C14:0), palmitic acid (hexadecanoic acid, C16:0), stearic acid (octadecanoic acid, C18:0), arachidic acid (eicosanoic acid, C20:0) and behenic acid (docosanoic acid C22:0).

In some specific embodiments, the saturated fatty acid residue is predominantly a palmitic acid residue.

In the various aspects and embodiments of the invention, in the vegetable-derived fat source according to the invention at least about 30%, at times, at least about 33%, at times, at least about 38%, and even, at times, at least about 40% of the total palmitic acid residues are present at the sn-2 position of the glycerol backbone.

In the various aspects and embodiments of the invention, in the vegetable-derived fat source according to the invention at least about 50%, at times, at least about 70% of the total fatty acid moieties at the sn-1 and sn-3 positions of the glycerol backbone are unsaturated.

The unsaturated fatty acid may be any one of oleic acid (C18:1), linoleic acid (C18:2), α-linolenic acid (C18:3) and gadoleic acid (C20:1).

In the various aspects and embodiments of the invention, in the vegetable-derived fat source according to the invention at least about 35%, at times, at least about 40% of the unsaturated fatty acid moieties at the sn-1 and sn-3 positions are oleic acid moieties.

In the various aspects and embodiments of the invention, in the vegetable-derived fat source according to the invention at least about 4%, at times, at least about 6% of the unsaturated fatty acid moieties at the sn-1 and sn-3 positions are linoleic acid moieties.

In the various aspects and embodiments of the invention, the vegetable-derived fat source is characterized by having the following parameters: (i) at least 30%, at times, at least 33%, at times, at least 38%, and even at times, at least 40% of the total palmitic acid residues are at the sn-2 position of the glycerol backbone; (ii) at least 50%, at times, at least 70% of the fatty acid moieties at the sn-1 and sn-3 positions of the glycerol backbone are unsaturated; (iii) at least 35%, at times, at least 40%, of the unsaturated fatty acid moieties at the sn-1 and sn-3 positions are oleic acid moieties; and (iv) at least 4%, at times, at least 6%, of the unsaturated fatty acid moieties at the sn-1 and sn-3 positions are linoleic acid moieties.

In the various aspects and embodiments of the invention, the vegetable-derived fat source comprises triglycerides with about 15% to about 40% palmitic acid moieties out of the total fatty acids. In some embodiments, the vegetable-derived fat source comprises triglycerides with about 15% to about 33% palmitic acid moieties out of the total fatty acids.

Thus, the palmitic acid content of the fat source may be 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54% or 55% of the total fatty acids.

In the various aspects and embodiments of the invention, in the vegetable-derived fat source according to the invention at least about 13% w/w, at times, at least about 15%, at times, at least about 18%, and even at times, at least about 22% of the total fatty acid residues at the sn-2 position of the glycerol backbone are palmitic acid residues.

A non-limiting example of a lipid composition or the vegetable-derived fat source according to all aspects of the invention comprises:
  0%—10%—C8:0 fatty acid residue out of the total fatty acid residue content;
  0%—10%—C10:0 fatty acid residue out of the total fatty acid residue content;
  0%—22%—C12:0 fatty acid residue out of the total fatty acid residue content;
  0%—15%—C14:0 fatty acid residue out of the total fatty acid residue content;
  15%—55%—C16:0 fatty acid residue out of the total fatty acid residue content;
  1%—7%—C18:0 fatty acid residue out of the total fatty acid residue content;
  20%—75%—C18:1 fatty acid residue out of the total fatty acid residue content;
  2%—40%—C18:2 fatty acid residue out of the total fatty acid residue content; and
  0%—8%—C18:3 fatty acid residue out of the total fatty acid residue content, and
wherein at least 30%, at times, at least 33%, and even at times, at least 40% of the C16:0 fatty acid residue out of the total fatty acid residue content is at sn-2 position the glycerol backbone.

In accordance with a more particular embodiment, the lipid composition or the vegetable-derived fat source according to all aspects of the invention comprises:
  0%—2%—C8:0 fatty acid residue out of the total fatty acid residue content;
  0%—2%—C10:0 fatty acid residue out of the total fatty acid residue content;
  5%—15%—C12:0 fatty acid residue out of the total fatty acid residue content;
  2%—10%—C14:0 fatty acid residue out of the total fatty acid residue content;
  17%—25%—C16:0 fatty acid residue out of the total fatty acid residue content;
  2%—5%—C18:0 fatty acid residue out of the total fatty acid residue content;
  28%—48%—C18:1 fatty acid residue out of the total fatty acid residue content;
  5%—20%—C18:2 fatty acid residue out of the total fatty acid residue content;
  1%—3%—C18:3 fatty acid residue out of the total fatty acid residue content; and
wherein at least 30%, at times, at least 33%, and even at times, at least 40% of the C16:0 fatty acid residue out of the total fatty acid residue content is at sn-2 position the glycerol backbone.

More specifically, the vegetable-derived fat source according to the invention comprises 0%—10% C8:0 fatty acids of the total fatty acids, preferably 0%—2%; 0%—10% C10:0 fatty acids of the total fatty acids, preferably 0%—2%; 0-22% C12:0 fatty acids of the total fatty acids, preferably 5-15%; 0-15% C14:0 fatty acids of the total fatty acids, preferably 2-10%; 15-55% C16:0 fatty acids of the total fatty acids, of which over 30% are esterified at the sn-2 position of the glycerol backbone; 1-7% C18:0 fatty acids of the total fatty acids, preferably 2-5%; 20-75% C18:1 fatty acids of the total fatty acids, preferably 28-48%; 2-40% C18:2 fatty acids of the total fatty acids, preferably 5-20%; 0-8% C18:3 fatty acids of the total fatty acids, preferably 1-3%; other fatty acids are each present in levels of less than 8% of the total fatty acids, preferably less than 5%.

Thus, the vegetable-derived fat source according to the invention may comprise: 0%, 1%, 2%, 3%, 4%, 5%, 6%, 7%, 8%, 9% or 10% of C8:0 fatty acids of the total fatty acids; 0%, 1%, 2%, 3%, 4%, 5%, 6%, 7%, 8%, 9% or 10% of C12:0 fatty acids of the total fatty acids; 0%, 1%, 2%, 3%, 4%, 5%, 6%, 7%, 8%, 9%, 10%, 11%, 12%, 13%, 14%, 15%, 16%, 17%, 18%, 19%, 20%, 21% or 22% of C12:0 fatty acids of the total fatty acids; 0%, 1%, 2%, 3%, 4%, 5%, 6%, 7%, 8%, 9%, 10%, 11%, 12%, 13%, 14% or 15% C14:0 fatty acids of the total fatty acids; 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54% or 55% C16:0 fatty acids of the total fatty acids; 1%, 1.2%, 1.4%, 1.6%, 1.8%, 2%, 2.2%, 2.4%, 2.6%, 2.8%, 3%, 3.2%, 3.4%, 3.6%, 3.8%, 4%, 4.2%, 4.4%, 4.6%, 4.8%, 5%, 5.2%, 5.4%, 5.6%, 5.8%, 6%, 6.2%, 6.4%, 6.6%, 6.8%, or 7% C18:0 fatty acids of the total fatty acids; 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% or 75% C18:1 fatty acids of the total fatty acids; 2%, 3%, 4%, 5%, 6%, 7%, 8%, 9%, 10%, 11%, 12%, 13%, 14%, 15%, 16%, 17%, 18%, 19%, 20%, 22%, 23%, 25%, 26%, 27%, 28%, 29%, 30%, 31%, 32%, 33%, 34%, 35%, 36%, 37%, 38%, 39%, 40% C18:2 fatty acids of the total fatty acids; 0%, 0.5%, 1%, 1.2%, 1.4%, 1.6%, 1.8%, 2%, 2.2%, 2.4%, 2.6%, 2.8%, 3%, 3.2%, 3.4%, 3.6%, 3.8%, 4%, 4.2%, 4.4%, 4.6%, 4.8%, 5%, 5.2%, 5.4%, 5.6%, 5.8%, 6%, 6.2%, 6.4%, 6.6%, 6.8%, 7%, 7.2%, 7.5%, 7.8% or 8% C18:3 fatty acids of the total fatty acids.

Specific vegetable-derived fat sources are described in WO05/036987 which is fully incorporated herein by reference. These include fat concentrates (fat bases), fat blends, infant formulas comprising the concentrates/blends and other foods and food articles.

Of particular interest are vegetable-derived fat sources which are based on edible synthetic oils (which can be enzymatically produced), which mimic, as are, or when blended with edible vegetable oils (which may be randomized before blending) the triglyceride composition of human breast milk fat. Such fat sources have a high level of palmitic acid at the sn-2 position of the triglycerides, and a high level of unsaturated fatty acids at sn-1 and sn-3 positions. Oils of this type are applicant's various products marked InFat™ (Enzymotec Ltd., Migdal HaEmeq, Israel). InFat™ is used by applicant for a wide selection of fat bases (fat concentrates) for use, when diluted/blended with vegetable oils, in the preparation of infant formulas, dietary supplements and food articles, and also for resulting blends. Examples of InFat™ compositions are shown in Table 1 below.

Thus, the vegetable-derived fat source used by the present invention may be a concentrate, particularly an enzymatically prepared fat base composition comprising a mixture of vegetable-derived triglycerides, with a total palmitic acid residues content of at most 38%, at times, at most 50%, of the total fatty acid residues; and with at least 50%, at times, at least 52.9%, even at times, at least 60% of the fatty acid moieties at the sn-2 position of the glycerol backbone being palmitic acid residues.

InFat™ is an advanced fat-base ingredient for the production of fat preparations used in infant nutrition and in infant formulas. It is an exclusive fat base, designed and manufactured with a specific triglyceride compositions and structures, which has now been found to be efficient in promoting development of gut flora, particularly in infant populations prone to problems related to gut flora, as well as other such populations.

Thus, in the various aspects and embodiments of the invention, the vegetable-derived fat source may be man-made, synthetically made, artificially made and/or enzymatically made.

Further, in the various aspects and embodiments of the invention, the vegetable-derived fat source and/or at least one triglyceride of the fat source may be selected from the group consisting of naturally occurring triglycerides, synthetic triglycerides, semi-synthetic triglycerides, and artificially produced triglycerides. In some further embodiments the triglyceride may be obtained from a vegetable source.

The vegetable-derived fat source according to the invention can also be a substitute human milk fat composition or human milk fat mimetic composition comprising a blend of at least 25% of the fat base concentrate with up to 75% of at least one vegetable oil. In some specific embodiments the fat source may comprise 25%, 30%, 36%, 50%, 52%, 60%, 63%, 73% and 83% of the fat base concentrate and 75%, 70%, 64%, 50%, 48%, 40%, 37%, 27% and 17%, respectively, of the at least one vegetable oil.

The following Examples present twelve blends, 1 to 12, wherein different amounts of the fat base concentrate (InFat™) were used, from 25% up to 83% of the content of the blend.

The vegetable oil used in the preparation of blends may be at least one of soy, palm tree, canola, coconut, palm kernel, sunflower, corn, safflower and rapeseed oil, as well as other vegetable oils and fats and mixtures thereof.

Thus, in the various aspects and embodiments of the invention, the vegetable-derived fat source comprises a fat base blended with a mixture of vegetable oils, wherein the mixture comprises oils selected from the group consisting of but not limited to soy, palm tree, canola, coconut, palm kernel, sunflower, corn, safflower and rapeseed oil. The vegetable oils (blending oils) may be chemically or enzymatically randomized before blending with the fat base (fat concentrate).

Most importantly, the vegetable-derived fat source of the present invention may be used in the preparation of infant formula. The infant formula used by the invention comprises in addition to the fat source at least one protein component and optionally at least one of carbohydrate source, vitamins, minerals, nucleotides and amino acids.

Thus, in the various aspects and embodiments of the invention, the infant formula comprises the vegetable-derived fat source, together with a protein source, a carbohydrate source, minerals, vitamins and optionally at least one of carrier, diluent, additive or excipient.

The terms "lipid" and "fat" are used herein synonymously.

The methods according to the invention are best practiced through administering to a subject, an infant formula or a food article prepared with and comprising the vegetable-derived fat source as described in the invention, either in the form of a concentrate base or in the form of a blend. Non-limiting examples of a fat concentrate/base are Fat Bases 1 to 11, and non-limiting examples of blends are Fat Blends 1 to 12.

Administration is usually via oral or enteral route, which may include the use of gavage feeding, with a gastric feeding tube, sonda, etc, particularly where adapted for infant feeding.

In another of its aspects, the present invention provides an edible vegetable-derived fat source for use in promoting development of beneficial gut flora in a subject, wherein the fat source is a triglyceride fat source comprising triglycerides with about 15 to about 55% palmitic acid moieties out of the total fatty acids, and wherein the level of palmitic acid moieties at the sn-2 position of the glycerol backbone is at least about 30% of total palmitic acid.

In some embodiments the vegetable-derived fat source has an effect on colonization of at least one pathogenic bacteria in the gut of the subject, wherein the effect is selected from the group consisting of inhibiting, preventing and reducing colonization of the at least one pathogenic bacteria.

In some embodiments the vegetable-derived fat source may have an effect to the immune system of the subject.

In some embodiments the fat source has an effect on the immune system of the subject, wherein the subject suffers from at least one disorder of the immune system resulting from gut flora imbalance.

In some embodiments the at least one disorder in the immune system may be selected from inflammation, atopy, allergy, feeding intolerance and infection and the lipid composition is effective to treat the disorder.

In some embodiments the atopy may be selected from the group consisting of allergy, asthma, eczema, rhinitis and atopic dermatitis.

In some embodiments the vegetable-derived fat source promotes development of gut flora comprising predominantly bifidobacteria and lactobacilli.

In some further embodiments the f vegetable-derived at source may enhance colonization (increase the abundance) of the at least one beneficial bacterium in the gut of the subject. The bacteria may be selected from the group consisting of bifidobacteria and *lactobacillus*.

In some embodiments the vegetable-derived fat source inhibits colonization of the at least one pathogenic bacteria in the gut of the subject.

In some embodiments the pathogenic bacteria is selected from the group consisting of coliform organisms, enterobacteria, *clostridia, veillonella*, proteus, *P. aeruginosa, clostridium, staphylococus* and streptococci. In some embodiments the pathogenic bacteria are *clostridium* and/or *staphylococcus*.

The lipid/fat source composition according to the invention may be formulated as or into an edible product. To this end, the lipid/fat source composition may be combined with at least one probiotic and prebiotic substance.

The edible product may be a nutritional composition, a pharmaceutical composition, a nutraceutical composition and/or a functional food. The edible product may be provided in fluid form (e.g. as a drink or beverage), as well as in a solid or semi solid form (e.g. as a porridge, or solid edible product).

The fat source according to the invention may be comprised in any one of food article and infant formula. The food article may be selected from bakery products, including bread, particularly biscuits and pastries, human milk fat substitute, dairy products, including milk and dairy drinks, ice cream, cereal products, sauces, soup, spreads, including margarine, fillings, oils and fats, soy products, meat products, fried food products, confectionery products, bars, candy bars, candies and chocolates, snacks, drinks and shakes, instant products, instant drink products, frozen food, prepared foods for infants, toddlers and young children, including prepared cooked mashed vegetables and/or fruits, condiment products, and cooking oils and fats.

Thus, in another of its aspects, the present invention provides a food article comprising the vegetable-derived fat source according to the invention for promoting development of beneficial gut flora in a subject, wherein said food article is selected from bakery products, including bread, particularly biscuits and pastries, human milk fat substitute, infant formula, dairy products, including milk and dairy drinks, ice cream, cereal products, sauces, soup, spreads, including margarine, fillings, oils and fats, soy products, meat products, fried food products, confectionery products, bars, candy bars, candies and chocolates, snacks, drinks and shakes, instant products, instant drink products, frozen food, prepared foods for infants, toddlers and young children and for adults, including prepared cooked mashed vegetables and/or fruits, condiment products, and cooking oils and fats.

In a further aspect, the invention relates to a commercial package for preparing an edible fat source or food article which is recommended for promoting development of beneficial gut flora in a subject and/or for reducing the frequency and duration of crying periods in a subject, in accordance with the invention. In addition to the active and non-active constituents, the commercial package contains instructions for use. These include terms of storage, instructions for preparation of the fat source or food article for administration, required dilutions, dosages, frequency of administration and the like. A commercial package in accordance with the invention may also contain the vegetable-derived fat source in a ready-to-use form, together with instructions for use. Dosages are usually determined according to age, weight, sex and condition of the subject, in accordance to good medical practice known to the attending physician and other medical personnel.

Thus, the present invention provides a commercial package comprising a) a vegetable-derived fat source which upon enteral administration to a subject it promotes development of beneficial gut flora in the subject;

b) optionally at least one of edible physiologically acceptable protein, carbohydrate, vitamin, mineral and active or non-active additive;

c) optionally at least one edible physiologically acceptable carrier or diluent for carrying the constituents defined in a) and b);

d) means and receptacles for admixing the constituents defined in a), b) and/or c); and e) instructions for use In yet a further aspect, the present invention provides a commercial package comprising:

a) a vegetable-derived fat source which upon enteral administration to a subject reduces the frequency and duration of crying periods in a subject, specifically an infant;

b) optionally at least one of edible physiologically acceptable protein, carbohydrate, vitamin, mineral and active or non-active additives;

c) optionally at least one edible physiologically acceptable carrier or diluent for carrying the constituent/s defined in a) and b);

d) means and receptacles for admixing the constituents defined in a), b) and/or c); and e) instructions for use.

In a specific embodiment of the commercial packages according to the invention, the vegetable-derived fat source is a triglyceride fat source comprising triglycerides with about 15% to about 55% palmitic acid moieties out of the total fatty acids, and wherein the level of palmitic acid moieties at the sn-2 position of the glycerol backbone is at least 30% of total palmitic acid.

In some embodiments the lipid composition may be artificially enriched with at least one triglyceride. As used herein, the term "artificially enriched" is used to denote that the lipid composition, while typically originated from a natural lipid source, is subjected to at least one modification, typically an enzymatic processing step, albeit not limited thereto, that promotes enrichment of the lipids with at least one triglyceride as defined.

The natural lipid source may be any edible lipid source, preferably, a vegetable oil, including, without being limited thereto, soy oil, palm tree oil, canola oil, coconut oil, palm kernel oil, sunflower oil, corn oil, safflower and rapeseed oil.

The lipid composition is preferably provided to the subject orally, e.g. as an edible product, as discussed herein.

The methods according to the invention may be short-term methods as well as long-term methods. In other words, the subject, in particular, the infant, toddler or child subject, may receive a single dose of the lipid composition or an edible product comprising the lipid composition, as well as a series of doses of the lipid composition, per day, a series of doses along a period of several days, weeks, months and 1, 2, 3 or more years. It is appreciated that when the methods according to the invention are conducted for a long period of time, the composition of the fat source and/or the product may vary depending on the age of the subject, as well as other considerations such as nutritional needs. Administration may commence at any time from day one after birth. Administration may also be to a breastfed subject, as supplementary feedings, or during or after weaning, or when the breastfeeding person (usually mother) is absent or unable to breastfeed.

Thus, the method of promoting development of beneficial gut flora in a subject provides for maintaining an advantageous gut flora profile, for example but not limited to the profile of the gut flora of a breastfed infant, baby or toddler.

In some embodiments the triglyceride according to the invention is selected from the group consisting of naturally occurring triglycerides, synthetic triglycerides semi-synthetic triglycerides, and artificially produced triglycerides, all derived from a vegetable source.

As used herein, the forms "a", "an" and "the" include singular as well as plural references unless the context clearly dictates otherwise. For example, the term "a triglyceride" includes one or more triglycerides which may form together a lipid base or a lipid blend. The term "consisting essentially of" is used to define the lipid composition which include the recited elements but exclude other elements, i.e. the term lipid composition is used to define a composition consisting essentially only lipids. "Consisting of" shall thus mean excluding more than trace elements of other elements. Embodiments defined by each of these transition terms are within the scope of this invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Further, all numerical values, e.g. when referring the amounts or ranges of the elements constituting the various lipid compositions herein are approximations which are varied (+) or (−) by up to 20%, at times by up to 10% of the stated values. It is to be understood, even if not always explicitly stated that all numerical designations are preceded by the term "about".

It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is noted that features of certain embodiments of the invention which are described in detail in the context of one aspect of the invention, may be applicable in other aspects of the invention.

The invention will now be exemplified in the following description of experiments that are carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described herein below.

DESCRIPTION OF NON-LIMITING EXAMPLES

In the present description as well as in the non-limiting examples provided below reference is made to fat bases and fat blends. It is to be understood that the term "fat base" or "fat concentrate" or "fat base concentrate" is used to denote the enzymatically prepared lipid composition comprising a mixture of vegetable-derived triglycerides with high sn-2 palmitic acid; while the term "fat blend" is used to denote a lipid composition comprising a fat base and a mixture of vegetable-derived triglycerides. The fat blend is at time referred to by the term "InFat". As shown below, the fat blend is a fat base comprising mainly triglycerides with oleic-palmitic-oleic (OPO) fatty acids, with high total palmitic and high sn-2 palmitic acid mixed with other vegetable oils. Generally, this fat blend is used as a fat fraction in infant formulas and can be used in other baby foods such as biscuits, bar, etc.

Example 1

Preparing Fat Bases and Fat Blends

Table 1 details the contents of several fat bases enriched with a high content of palmitic acid at the sn-2 position. The fat bases comprise a high percentage of palmitic acid, C16:0, at the sn-2 position of triacylglycerol (TAG), and high percentage of unsaturated fatty acids at the sn-1 and sn-3 positions.

The fat bases are prepared as described in WO05/036987 which publication is fully incorporated herein by reference. Generally, a mixture of triglycerides, rich in palmitic acid (preferably above 78%) are reacted with a mixture of free fatty acids rich in oleic acid (preferably above 75%), with a low content of palmitic and stearic acids (preferably below 6%).

Briefly, the triglyceride mixture may be produced from double-fractioned palm stearin and the free fatty acids (FFA) mixture is obtained from palm kernel oil after fractionation, or from high oleic sunflower oil. The two mixtures are blended in stirred (optionally large scale) reactors with no additional solvent. To this mixture is added a suitable lipase and the mixture of triglycerides, FFA and catalyst is stirred at 50° C.-60° C. for about 3-9 hours, to yield the final and desired triglycerides mixture. Any excess FFAs are removed.

The triglyceride product may be further treated in order to improve color, odor and taste with bleaching and deodorization stages. Optionally, the product is fortified with natural antioxidants to increase the shelf life of the product. The catalyst can be further recycled, to be re-used in further batches.

TABLE 1

Fat bases composition

| fatty acid* | Fat Base No. | | | | | | | | | | |
|---|---|---|---|---|---|---|---|---|---|---|---|
| | 1 | 2 | 3 | 4 | 5 | 6 | 7 | 8 | 9 | 10 | 11 |
| C16:0 | 32 | 29.4 | 29.6 | 32.6 | 32.2 | 30.6 | 29 | 29 | 30 | 33 | 30 |
| C16:0 at sn-2 of total fatty acids at sn-2 | 67.2 | 59.7 | 61.3 | 66.1 | 66 | 62.9 | 53.9 | 55.6 | 59 | 52.9 | 55.8 |
| Ratio (%) of C16:0 at sn-2 out of total C16:0 | 70.0 | 67.7 | 69.0 | 67.6 | 68.3 | 68.5 | 62 | 64 | 64 | 53.5 | 62 |
| C18:0 | 4 | 4.4 | 4.4 | 4 | 4.1 | 3.8 | 2.6 | 2.6 | 3 | 3 | 3 |
| C18:1 | 53.1 | 55.9 | 55.5 | 53.1 | 53.4 | 55 | 55.5 | 56 | 56.1 | 52 | 56.1 |
| C18:2 | 8 | 7.8 | 8.2 | 8 | 7.9 | 8.3 | 9 | 9 | 8.5 | 10 | 8.5 |

*All numbers represent % (w/w), except the ratio which is defined as %. "C16:0" represents the total palmitic acid content out of total fatty acids. "C16:0 at sn-2" represents the % palmitic acid at sn-2 out of total sn-2 positioned fatty acids. "Ratio" represents % of C16:0 at sn-2 palmitic acid out of total C16:0 [(% of C16:0 at sn-2 out of total sn-2 positioned fatty acids)/3)/(% total C16:0)] × 100

The fat bases are then used to form the fat blends which comprise also other oils. The fat base may represent from about 30% up to about 83% of the fat blends suitable for use in a formula for use in the invention. The blends comprising the fat bases of Table 1 in combination with other fats are provided in Table 2.

Specifically, Table 2 details the contents of blends comprising one of fat bases 1, 7, 8, 9, 10 or 11. The fat blends are prepared by blending the selected fat base with other oils. As such, the fatty acids composition of the blends results from the fatty acids composition of both the fat base and of the other oils mixed with the fat base.

TABLE 2

Fat blends composition

| fat* | Fat Blend No. | | | | | | | | | |
|---|---|---|---|---|---|---|---|---|---|---|
| | Fat blend 1 | Fat blend 2 | Fat blend 3 | Fat blend 4 | Fat blend 5 | Fat blend 6 | Fat blend 7 | Fat blend 8 | Fat blend 9 | Fat blend 10 |
| C12:0 | 11.1 | 7.2 | 7.8 | 6.5 | 4.4 | 8.14 | 8.7 | 13.4 | 10.4 | 10 |
| C14:0 | 4.5 | 3.1 | 3.3 | 2.8 | 2.1 | 2.94 | 3.54 | 5.3 | 4.3 | 4.2 |
| C16:0 | 22.8 | 25.4 | 26.9 | 25.1 | 27.7 | 21.60 | 20.99 | 15 | 22.3 | 17 |
| C16:0 at sn-2 of total fatty acids at sn-2 | 33.4 | 42.9 | 48.9 | 50.8 | 56.9 | 31.3 | 31.8 | 25 | 28.8 | 16 |
| Ratio (%) sn-2 C16:0 of total C16:0 | 48.7 | 56.3 | 60.7 | 67.4 | 68.5 | 48.31 | 50.46 | 55 | 43 | 31.5 |
| C18:0 | 2.3 | 3.0 | 3.1 | 3.5 | 4.0 | 2.65 | 2.65 | 2.9 | 4.4 | 3.2 |
| C18:1 | 38.4 | 40.8 | 41.6 | 47.9 | 46.6 | 42.71 | 44.37 | 39.7 | 38.5 | 41.7 |
| C18:2 | 13.5 | 15.6 | 12.8 | 8.6 | 11.7 | 17.96 | 16.43 | 15.3 | 14.0 | 18.2 |
| C18:3 | 1.7 | 0.6 | | 1.4 | | 1.69 | 1.52 | 2 | 1.5 | 2.1 |
| % Fat base 1 | 30 | 50 | 63 | 73 | 83 | | | | | |
| % Fat base 7 | | | | | | 60 | | | | |
| % Fat base 8 | | | | | | | 60 | | | |
| % Fat base 9 | | | | | | | | 36 | | |
| % Fat base 10 | | | | | | | | | 52 | |
| % Fat base 11 | | | | | | | | | | 25 |

TABLE 2-continued

Fat blends composition

| fat* | Fat blend 1 | Fat blend 2 | Fat blend 3 | Fat blend 4 | Fat blend 5 | Fat blend 6 | Fat blend 7 | Fat blend 8 | Fat blend 9 | Fat blend 10 |
|---|---|---|---|---|---|---|---|---|---|---|
| Vegetable Oil | | | | | | | | | | |
| Palm kernel oil | | | | | | 18 | | | | |
| Coconut oil | 23 | 15 | 16 | 13.5 | 9.3 | | 17 | 28 | 21 | 21 |
| Palm oil | 21 | 15 | 9 | | | | | | | 14 |
| Sunflower | | 5 | | | 7.7 | | | 11 | | 14 |
| Corn oil | 10 | 10 | 12 | | | | | | 11 | |
| Safflower | | | | | | | | 3 | | 5 |
| Rapeseed | 16 | 5 | | 13.5 | | 4 | 6 | 20 | 16 | 21 |
| Soybean | | | | | | 18 | 17 | | | |
| Total | 100 | 100 | 100 | 100 | 100 | 100 | 100 | 100 | 100 | 100 |

*All numbers represent % (w/w), except the ratio which is defined as %. "C16:0" represents the total palmitic acid content of total fatty acids. "C16:0 at sn-2" represents the % palmitic acid at sn-2 out of total sn-2 positioned fatty acids. "Ratio" represents % of C16:0 at sn-2 palmitic acid out of total C16:0 [(% of C16:0 at sn-2 out of total sn-2 positioned fatty acids)/3)/(% total C16:0)] × 100

TABLE 3

Fat blend 11 composition (with 30% fat base)

| Fatty acid | % of fatty acids |
|---|---|
| C10:0 | 1.3 |
| C12:0 | 10.3 |
| C14:0 | 4.3 |
| C16:0 | 23.5 |
| C16:0 at sn-2 of total fatty acids at sn-2 | 30.3 |
| Ratio (%) of C16:0 at sn-2 of total C16:0 | 43 |
| C18:0 | 3.2 |
| C18:1 | 39.2 |
| C18:2 | 13.6 |
| C18:3 | 1.7 |
| C20:0 | 0.3 |
| C20:1 | 0.3 |
| C22:0 | 0.2 |
| % fat base in fat blend 11 | 30 |

*All numbers represent % (w/w), except the ratio which is defined as %. "C16:0" represents the total palmitic acid content of total fatty acids. "C16:0 at sn-2" represents the % palmitic acid at sn-2 out of total sn-2 positioned fatty acids. "Ratio" represents % of C16:0 at sn-2 palmitic acid out of total C16:0 [(% of C16:0 at sn-2 out of total sn-2 positioned fatty acids)/3)/(% total C16:0)] × 100

TABLE 4

Fat Blend 12 composition (with 43% fat base)

| Fatty acid | % from total Fatty acids |
|---|---|
| C8:0 | 1.6 |
| C10:0 | 1.5 |
| C12:0 | 10.6 |
| C14:0 | 3.9 |
| C16:0 | 17.2 |
| C16:0 at sn-2 of total fatty acids at sn-2 | 26.3 |
| Ratio (%) of sn-2 palmitic acid of total palmitic acid | 51 |
| C18:0 | 2.4 |
| C18:1 | 41.1 |
| C18:2 | 18.2 |
| C18:3 | 2.2 |
| % fat base (concentrate) in fat blend | 43 |
| Vegetable Oil | |
| Randomized Coconut oil | 22 |
| Randomized Sunflower | 15 |
| Randomized Rapeseed | 20 |

*All numbers represent % (w/w), except the ratio which is defined as %. "C16:0" represents the total palmitic acid content of total fatty acids. "C16:0 at sn-2" represents the % palmitic acid at sn-2 out of total sn-2 positioned fatty acids. "Ratio" represents % of C16:0 at sn-2 palmitic acid out of total C16:0 [(% of C16:0 at sn-2 out of total sn-2 positioned fatty acids)/3)/(% total C16:0)] × 100

Example 2

Infant Formula Preparation

The infant formulas comprising a lipid composition (fat blend) were prepared as follows:

The fat fraction (fat blend) produced by the blending of fat base with other oils and fats as described above was further blended with other nutrients such as proteins, minerals, vitamins and carbohydrates to yield a food product supplying an infant with the major nutrients also found in human milk. The nutrients and fats were homogenized using pressure homogenization and spray dried to yield a homogenous powder. The powder was further re-dispersed in water (approx. 9 g powder per 60 ml water) to yield a ready-to-feed formula. The fat content of the ready feed was approx. 3.5 g per 100 ml which corresponds to the fat content of human breast milk, which is in the range of 30-40 g/L.

Fat blend 9 was then mixed with other components as detailed in Table 5 below to form infant formulas based on Fat Blend 9.

TABLE 5

Composition of the infant formula based on Fat Blend 9

| Formula | Per 100 g powder | Per 100 ml ready to feed (after mixing 15 gr in 100 ml water) |
|---|---|---|
| Energy/Calories (kcal) | 510 | 76.5 |
| Sodium (mg) | 160 | 24.0 |

TABLE 5-continued

Composition of the infant formula based on Fat Blend 9

| Formula | Per 100 g powder | Per 100 ml ready to feed (after mixing 15 gr in 100 ml water) |
|---|---|---|
| Protein (g) (Lactalbumin/Casein 60/40) | 12 | 1.8 |
| Total Fat Blend in Infant Formula (gr) | 26 | 3.9 |
| Total Saturated fat (gr) | 11 | 1.7 |
| Linoleic acid (mg) | 3540 | 531.0 |
| Alpha-linolenic acid (mg) | 355 | 53.3 |
| Arachidonic acid (mg) | 99 | 14.9 |
| Docosahexaenoic acid (mg) | 99 | 14.9 |
| Cholesterol (mg) | 27 | 4.1 |
| Lactose (gr) | 57 | 8.6 |
| Calcium (mg) | 455 | 68.3 |
| Phosphorus (mg) | 235 | 35.3 |
| Potassium (mg) | 410 | 61.5 |
| Chloride (mg) | 285 | 42.8 |
| Iron (mg) | 5.1 | 0.8 |
| Magnesium (mg) | 53 | 8.0 |
| Zinc (mg) | 3.5 | 0.5 |
| Copper (mcg) | 260 | 39.0 |
| Manganese (mcg) | 25 | 3.8 |
| Iodine (mcg) | 77 | 11.6 |
| Taurine (mg) | 37 | 5.6 |
| Vitamin A I.U. | 1570 | 235.5 |
| Vitamin D I.U. | 365 | 54.8 |
| Vitamin E (mg) | 7.5 | 1.1 |
| Vitamin K (mcg) | 59 | 8.9 |
| Vitamin C (mg) | 99 | 14.9 |
| Vitamin $B_1$ (mcg) | 550 | 82.5 |
| Vitamin $B_2$ (mcg) | 1660 | 249.0 |
| Vitamin $B_6$ (mcg) | 420 | 63.0 |
| Vitamin $B_{12}$ (mcg) | 3.3 | 0.5 |
| Niacin (mg) | 6.8 | 1.0 |
| Panthothenic acid (mg) | 5.6 | 0.8 |
| Folic acid (mcg) | 92 | 13.8 |
| Biotin (mcg) | 17 | 2.6 |
| Choline (mg) | 115 | 17.3 |
| Inositol (mg) | 46 | 6.9 |
| Moisture % | 3 | |

Similarly, another infant formula was prepared using fat blend 11, as detailed in Table 6 below.

TABLE 6

Composition of the infant formula based on Fat Blend 11

| Formula | Per 100 g powder | Per 100 ml ready to feed (after mixing 15 gr in 100 ml water) |
|---|---|---|
| Energy/Calories (kcal) | 508 | 68 |
| Sodium (mg) | 140 | 18.8 |
| Protein (g) (Lactalbumin/Casein 60/40) | 11.4 | 1.5 |
| Total Fat Blend in Infant Formula (gr) | 26.5 | 3.5 |
| Total Saturated fat (gr) | 11.3 | 1.49 |
| Linoleic acid (mg) | 5000 | 670 |
| Alpha-linolenic acid (mg) | 530 | 71 |
| Arachidonic acid (mg) | 115 | 15.3 |
| Docosahexaenoic acid (mg) | 108 | 14.4 |
| Cholesterol (mg) | 2 | 0.3 |
| Lactose (gr) | 56 | 7.5 |
| Calcium (mg) | 430 | 57.3 |
| Phosphorus (mg) | 250 | 33.5 |
| Potassium (mg) | 420 | 56.3 |
| Chloride (mg) | 300 | 40.2 |
| Iron (mg) | 5.25 | 0.7 |
| Magnesium (mg) | 50 | 6.7 |
| Zinc (mg) | 3.5 | 0.47 |
| Copper (mcg) | 300 | 40.2 |
| Manganese (mcg) | 45 | 6 |
| Iodine (mcg) | 45 | 6 |
| Taurine (mg) | 45 | 6 |
| Vitamin A I.U. | 1500 | 200 |
| Vitamin D I.U. | 300 | 40.2 |
| Vitamin E (mg) | 10 | 1.3 |
| Vitamin K (mcg) | 45 | 6 |
| Vitamin C (mg) | 60 | 8 |
| Vitamin $B_1$ (mcg) | 400 | 53 |
| Vitamin $B_2$ (mcg) | 800 | 127 |
| Vitamin $B_6$ (mcg) | 375 | 50 |
| Vitamin $B_{12}$ (mcg) | 1.15 | 0.2 |
| Niacin (mg) | 6 | 0.8 |
| Panthothenic acid (mg) | 3 | 0.4 |
| Folic acid (mcg) | 67 | 9 |
| Biotin (mcg) | 14.3 | 1.9 |
| Choline (mg) | 37.5 | 5 |
| Inositol (mg) | 22.5 | 3 |
| Moisture % | 3 | |

The level of fat in an infant formula and the exact composition of the fat blend can be controlled in order to yield a final formulation which optimally mimics the human milk fat at different lactation periods. Generally, as appreciated, composition of mammalian milk changes in terms of fat content during lactation stages (set according to the age of the infant) and the infant formula, and in particular, the fat blend content, may thus be adapted according to the desired stage that needs to be mimicked.

Example 3

The Effect of Infant Formula with Different Fat Components on Intestinal Flora in Formula-Fed Infants Study Design The effect of the fat component in the infant formula on intestinal flora was examined in a double blind randomized clinical trial in human term formula fed infants with a reference arm of human breastfed infants.

Following screening, 36 healthy, growing, term infants were randomized to one of two treatment groups, 8 infants in the control group and 14 in the InFat group, with additional 14 breastfed infants as reference.

Diets

The efficacy of infant formula with fat blend 9 was investigated in a double-blind, randomized, controlled 6 weeks duration trial in healthy term infants. The study demonstrated the effect of the infant formula with InFat blend 9 compared to infant formula with standard vegetable oil (having high total palmitic mostly at sn-1 and sn-3 positions) and to breastfed milk, on intestinal microflora in term infants.

The three study groups were:

Group I—the InFat group, infants fed with the infant formula comprising InFat blend No. 9, enriched with palmitic acid at the sn-2 position;

Group II—the control group, infants fed with the vegetable oil mixture which comprises the same total amount of palmitic acid but mostly esterified to sn-1 and sn-3 positions;

Group III—the reference breastfeeding group, infants being breastfed.

The InFat infant formula (of Group I) and the control infant formula (of Group II) were essentially similar with respect to nutrient content and differ only in the position of palmitic acid in the triglyceride. Both the formula of Group I and the formula of Group II do not include any probiotics or prebiotics.

TABLE 7

Fatty acids composition comparison between tested Groups (% of weight of total fatty acids)

| Fatty acid | Group I InFat based Infant Formula | Group II Vegetable oil mix based infant formula | Group III Human milk (Jensen 1999*) |
|---|---|---|---|
| C8:0 | 0.9 | 3.0 | |
| C10:0 | 0.8 | 2.2 | 0.05-2.21 |
| C12:0 | 10.4 | 9.4 | 2.01-11.77 |
| C14:0 | 4.3 | 4.2 | 2.26-11.68 |
| C16:0 | 22.3 | 18.7 | 12.9-27.50 |
| Ratio of C16:0 at sn-2 position of total C16 | 43 | 13.6 | ~70 |
| C18:0 | 4.4 | 6.4 | 3.49-10.65 |
| C18:1 | 38.5 | 34.4 | 23.55-55.25 |
| C18:2 | 14.0 | 15.1 | 5.79-27.55 |
| C18:3 | 1.5 | 1.5 | 0.25-1.9 |
| C20:4 | 0.5 | 0.4 | 0.05-0.87 |
| C22:6 | 0.4 | 0.4 | 0-1.03 |

*Jensen, R. G. Lipids 34(12): 1243-71, 1999

Gut Flora Evaluation

Intestinal flora: Stool samples of at least 1 gr were collected from each infant in the study at baseline (inclusion to the study) and after 6 weeks. Samples were stored at 4° C. for up to 24 hrs before examination.

The tests performed on each sample included specific bacterial counts on specific plates for a general estimation of different bacteria types such as:
1. *Lactobacillus* on MRS+cys plate
2. Bifidobacteria on MRS+++plate
3. *Staphylococcus* on BP plate
4. *Clostridium* on SPS plate
5. *Pseudomonas* on pseudo-cent plate Further, parents were asked to fill a 3 days diary of their infant feedings and significant crying periods. Additionally, each infant was monitored for anthropometric parameters, general health and well being for safety assessment.

Results 30 healthy, growing, term infants completed the 6 weeks study without protocol violation, 7 infants in the control group and 11 in the InFat group, with additional 12 breastfed infants as reference.

Both formulas were well tolerated, safe and did not produce any significant negative effect in the tested parameters.

Feeding

Infants that were fed with infant formula with InFat™ had less feedings per day at age of 6 weeks compared to infants that were fed with formula with standard vegetable oil (8 vs. 7.5 periods per day). Though, the amount of formula that was consumed was lower for the infants that were fed with infant formula with InFat™, the amount per feeding was higher compared to infants that were fed with formula with standard vegetable oil.

TABLE 8

Formula consumption

| | Control (n = 7) | | InFat (n = 11) | | significance 2 formula groups |
|---|---|---|---|---|---|
| | Mean | SEM* | Mean | SEM* | |
| formula consumption per day (ml/feeding) | 740.0 | 66.1 | 588.3 | 117.3 | .350 |
| formula consumption per kg per day | 150.0 | 10.0 | 133.0 | 26.0 | .599 |
| number of feedings per day | 8.0 | .5 | 7.5 | .8 | .614 |
| ml formula per feeding | 94.0 | 9.2 | 119.0 | 6.7 | .039 |

*SEM = standard error of the mean

Intestinal Flora

Infants that were fed with infant formula with InFat™ had intestinal flora with higher abundance of *lactobacillus* and bifidobacteria after 6 weeks of feeding compared to infants that were fed with formula with standard vegetable oil and comparable to that of infants that were breastfed.

Infants that were fed with infant formula with InFat™ had intestinal flora with decreased abundance of pathogenic bacteria such as *clostridia* after 6 weeks of feeding compared to infants that were fed with formula with standard vegetable oil and comparable to that of infants that were breastfed.

TABLE 9

Results of beneficial bacteria count (the results are graphically presented in FIG. 1)
Beneficial Bacteria

| | Control (n = 7) | | InFat (n = 11) | | Breastfed (n = 12) | | significance | |
|---|---|---|---|---|---|---|---|---|
| | Mean | SEM* | Mean | SEM* | Mean | SEM* | 3 groups | 2 formula-fed groups |
| *Lactobacillus* counts at baseline | 1.1E+09 | 6.5E+08 | 6.1E+09 | 3.2E+09 | 3.4E+09 | 1.8E+09 | .065 | .020 |
| *Lactobacillus* counts after 6 weeks feeding | 1.2E+10 | 3.2E+09 | 1.2E+11 | 7.8E+10 | 5.6E+10 | 2.0E+10 | .000 | .001 |
| Fold change of *Lactobacillus* from baseline | 11.2 | | 18.8 | | 16.6 | | | |
| *Bifidobacteria* counts at baseline | 1.5E+11 | 9.8E+10 | 5.2E+10 | 4.5E+10 | 1.6E+09 | 7.1E+08 | .000 | .291 |

TABLE 9-continued

Results of beneficial bacteria count (the results are graphically presented in FIG. 1)
Beneficial Bacteria

|  | Control (n = 7) | | InFat (n = 11) | | Breastfed (n = 12) | | significance | |
|---|---|---|---|---|---|---|---|---|
|  | Mean | SEM* | Mean | SEM* | Mean | SEM* | 3 groups | 2 formula-fed groups |
| Bifidobacteria counts after 6 weeks feeding | 5.1E+09 | 1.2E+09 | 1.2E+11 | 7.8E+10 | 3.9E+10 | 2.3E+10 | .000 | .000 |
| Fold change of Bifidobacteria from baseline | 0.0 | | 2.4 | | 25.1 | | | |

*SEM = standard error of the mean

TABLE 10

Results of pathogenic bacteria count
Pathogenic Bacteria

|  | Control (n = 7) | | InFat (n = 11) | | Breastfed (n = 12) | | significance | |
|---|---|---|---|---|---|---|---|---|
|  | Mean | SEM* | Mean | SEM* | Mean | SEM* | 3 groups | 2 formulas-fed groups |
| Clostridium counts at baseline | 3.3E+07 | 3.3E+07 | 9.1E+10 | 6.1E+10 | 4.3E+10 | 4.2E+10 | | .000 |
| Change of Clostridium counts from baseline | 2.1E+07 | 2.1E+07 | −9.1E+10 | 6.1E+10 | −3.4E+10 | 4.3E+10 | .463 | .258 |

*SEM = standard error of the mean

Comfort and Stool Characteristics

Parents of infants that were fed with infant formula with InFat™ did not report any significant difference of their infant stool characteristics or comfort compared to those of infants that were fed with formula with standard vegetable oil.

Crying

Infants that were fed with infant formula with InFat™ had less significant crying periods at age of 6 weeks compared to infants that were fed with formula with standard vegetable oil (0.49 vs. 0.8 periods per day or 1.5 vs. 2.4 crying periods per 3 days).

Conclusion

Infants that were fed with infant formula with InFat™ demonstrated:

Intestinal flora that was similar to that of infants that were breastfed and more favorable compared to that of infants fed infant formula with standard vegetable oil.

Reduced number of significant crying periods that was not related to reduction in hard stools or to comfort as no significant difference in the infant's stool characteristics or comfort was observed in comparison with the control group.

Example 4

The Effect of Infant Formula with Different Fat Components on Intestinal Flora in Infants Born by Caesarean Section Study Design The effect of the fat component in the infant formula on intestinal flora was examined in a clinical trial in human term formula fed infants born by Caesarean Section, known to be prone to intestinal flora which is not optimal, with a reference arm of human breastfed infants.

Following screening, 4 healthy, growing, term infants born by cesarean delivery were fed with infant formula with InFat™, with additional 4 breastfed infants as reference.

Diets

The efficacy of infant formula with fat blend 9 was investigated in a double-blind, randomized, controlled 6 weeks duration trial in healthy term infants. The study demonstrated the effect of the infant formula with InFat™ blend 9 (the formula as in example 3) compared to breastfed milk, on intestinal microflora in term infants.

The two study groups were:

Group I—the InFat™ group, infants fed with the infant formula comprising InFat blend No. 9, enriched with palmitic acid at the sn-2 position;

Group II—the reference breastfeeding group, infants being breastfed.

The formula of Group I did not include any probiotics or prebiotics.

Gut Flora Evaluation

Intestinal flora was evaluated as detailed in example 3.

Results

Intestinal Flora

Infants born by cesarean section that were fed with infant formula with InFat™ had intestinal flora with higher abundance of lactobacillus and bifidobacteria after 6 weeks of feeding compared to baseline and comparable to that of infants born by cesarean section that were breastfed.

TABLE 11

Results of beneficial bacteria count
Beneficial Bacteria

|  | InFat (n = 4) | | Breastfed (n = 4) | | significance 2 groups |
| --- | --- | --- | --- | --- | --- |
|  | Mean | SEM* | Mean | SEM* |  |
| Lactobacillus counts at baseline | 7.5E+08 | 5.8E+08 | 2.3E+09 | 1.6E+09 | 0.22 |
| Change of Lactobacillus counts from baseline | 1.1E+09 | 7.8E+08 | 4.1E+10 | 3.1E+10 | 0.236 |

*SEM = standard error of the mean

Infants that were fed with infant formula with InFat™ had intestinal flora with decreased abundance of pathogenic bacteria as *clostridia* and *staphylococcus* after 6 weeks of feeding compared to baseline and comparable to that of infants that were breastfed.

TABLE 12

Results of pathogenic bacteria count
Pathogenic Bacteria

|  | InFat (n = 4) | | Breastfed (n = 4) | | significance 2 groups |
| --- | --- | --- | --- | --- | --- |
|  | Mean | SEM* | Mean | SEM* |  |
| Clostridium counts at baseline | 1.3E+11 | 1.2E+11 | 1.3E+11 | 1.2E+11 | 0.991 |
| Change of Clostridium counts from baseline | −1.2E+11 | 1.3E+11 | −1.3E+11 | 1.2E+11 | 0.998 |
| Staphylococcus counts at baseline | 1.3E+11 | 1.2E+11 | 7.9E+09 | 5.3E+09 | 0.008 |
| Change of Staphylococcus counts from baseline | −1.3E+11 | 1.2E+11 | −7.8E+09 | 5.3E+09 | 0.384 |
| Pseudomonas counts at baseline | 1.3E+11 | 1.2E+11 | 6.9E+09 | 6.7E+09 | 0.016 |
| Change of Pseudomonas counts from baseline | −1.3E+11 | 1.2E+11 | −6.3E+09 | 6.8E+09 | 0.375 |

*SEM = standard error of the mean

Crying

Infants that were fed with infant formula with InFat™ had crying periods and duration at age of 6 weeks comparable to those of breastfed infants (0.67 and 0.8 crying periods per day and 10.4 and 19.4 minutes per day, respectively).

Conclusion

Infants born by Cesarean Section that were fed with infant formula with InFat™ demonstrated similar change in the intestinal flora to that of infants born by Cesarean Section that were breastfed; the pathogenic bacteria were reduced and the beneficial bacteria were increased.

Example 5

The Effect of Infant Formula with Different Fat Components on Crying in Formula-Fed Infants Study Design The effect of the fat component in the infant formula on crying duration and frequency was examined in a double blind randomized clinical trial in human term formula fed infants with a reference arm of human breastfed infants.

Following screening, 83 healthy, growing, term infants were randomized to one of two treatment groups, 28 infants in the control group and 30 in the InFat group, with additional 25 breastfed infants as reference.

Diets

The efficacy of infant formula with fat blend 9 was investigated in a double-blind, randomized, controlled 12 weeks duration trial in healthy term infants. The study demonstrated the effect of the infant formula with InFat blend 9 compared to infant formula with standard vegetable oil (having high total palmitic mostly at sn-1 and sn-3 positions) and to breastfed milk, on crying time in term infants.

The three study groups were:

Group I—the InFat group, infants fed with the infant formula comprising InFat blend No. 9, enriched with palmitic acid at the sn-2 position;

Group II—the control group, infants fed with the vegetable oil mixture which comprises the same total amount of palmitic acid but mostly esterified to sn-1 and sn-3 positions;

Group III—the reference breastfeeding group, infants being breastfed.

The InFat infant formula (of Group I) and the control infant formula (of Group II) were essentially similar with respect to nutrient content and differ only in the position of palmitic acid in the triglyceride. Both the formula of Group I and the formula of Group II do not include any probiotics or prebiotics.

Crying Evaluation

During the 12 weeks study parents were asked to fill 3 days diary of their infant feedings and significant crying periods at age of 6 weeks and at age of 12 weeks.

Results 66 healthy, growing, term infants completed the 12 weeks study, 21 infants in the control group and 23 in the InFat group, with additional 22 breastfed infants as reference.

Both formulas were well tolerated, safe and did not produce any significant negative effect in the tested parameters.

Comfort and Stool Characteristics

Infants that were fed with infant formula with InFat™ had stool characteristics that did not differ significantly from those of infants that were fed with formula with standard vegetable oil at age of 6 weeks (9.6% and 10.4% hard stools, respectively, p=0.6) and at age of 12 weeks (8.5% and 12.5% hard stools, respectively, p=0.3).

Parents of infants that were fed with infant formula with InFat™ did not report any significant difference of their infant stool characteristics or comfort compared to those of infants that were fed with formula with standard vegetable oil.

Crying

Infants that were fed with infant formula with InFat™ had statistically significant reduced crying time and frequency.

At age of 6 weeks infants that were fed with infant formula with InFat™ had statistically significant reduced number of crying periods compared to infants that were fed with infant formula with standard vegetable oil.

At age of 12 weeks infants that were fed with infant formula with InFat™ had statistically significant reduced crying duration and number of crying periods compared to infants that were fed with infant formula with standard vegetable oil.

The results also show that infants that were fed with infant formula with InFat™ had larger reduction in crying time per day from age of 6 weeks to age of 12 weeks.

TABLE 13 crying pattern at 6 and 12 weeks

|  | Control | | InFat ™ | | Statistical significance 2 formula groups |
| --- | --- | --- | --- | --- | --- |
|  | Mean | SEM* | Mean | SEM* |  |
| 6 weeks | n = 24 | | n = 26 | | |
| number of significant crying periods per day | 1.3 | 0.27 | 0.7 | 0.14 | 0.083 |
| 12 weeks | n = 21 | | n = 23 | | |
| number of significant crying periods per day | 0.8 | 0.17 | 0.3 | 0.06 | 0.033 |
| total crying duration per day (minutes) | 23.6 | 5.15 | 3.8 | 0.79 | 0.043 |
| Change in crying duration from 6 to 12 weeks | −4.8 | −1.05 | −32.1 | −6.69 | 0.12 |

*SEM = standard error of the mean

This reduction in crying was not related to hard stools and comfort since no statistical significance was shown for the hard stool reduction.

Conclusion

Infants that were fed with infant formula with InFat™ demonstrated reduced number of significant crying periods per day and reduced daily crying time duration.

Example 6

The Effect of Infant Formula with Different Fat Components on Immune Effects in Healthy Formula-Fed Infants Study Design The effect of the fat component in the infant formula on immune effect is examined in a double blind randomized clinical trial in human term formula fed infants with a reference arm of human breastfed infants.

Following screening, growing, term infants are randomized to one of two treatment groups, with additional breastfed infants as reference.

Diets

The efficacy of infant formula with InFat is investigated in a double-blind, randomized, controlled trial in healthy term infants. The study demonstrates the effect of the infant formula with InFat compared to infant formula with standard vegetable oil (having high total palmitic mostly at sn-1 and sn-3 positions) and to breastfed milk, on immune health in term infants.

The three study groups are:

Group I—the InFat group, infants fed with the infant formula comprising InFat, enriched with palmitic acid at the sn-2 position;

Group II—the control group, infants fed with the vegetable oil mixture which comprises the same total amount of palmitic acid but mostly esterified to sn-1 and sn-3 positions;

Group III—the reference breastfeeding group, infants being breastfed.

The InFat infant formula (of Group I) and the control infant formula (of Group II) are essentially similar with respect to nutrient content and differ only in the position of palmitic acid in the triglyceride.

Immune Health Evaluation

Immune health consists of few elements:
1. incidence of allergy or atopy
2. incidence of infectious episodes
3. immune response to regular vaccination Data is collected through follow-up visits, diaries written by parents, and telephone calls by trained personal.

In general, any sign or symptom related to allergy (Atopic dermatitis, wheezing episodes, and allergic urticaria) and infection (fever, cough, runny nose, and watery stools) is recorded, as well as any medical document.

During the study, parents are instructed to record allergic and infectious symptoms, every episode of fever, clinic visits, tests, physician's diagnosis, prescription of medications, particularly antibiotics, etc.

Additionally, each infant is monitored for anthropometric parameters, general health and well being.

Example 7

The Effect of Infant Formula with Different Fat Components on Protection from Allergy in Formula-Fed Infants Prone to Allergy Study Design The protective effect of the fat component in the infant formula against allergy and infections is examined in a prospective double blind randomized clinical trial in human term formula fed infants with a parental history of atopy and with a reference arm of human breastfed infants with a parental history of atopy.

Diets

The efficacy of infant formula with InFat is investigated in a double-blind, randomized, controlled trial in healthy term infants. The study demonstrates the protective effect of the infant formula with InFat compared to infant formula with standard vegetable oil (having high total palmitic mostly at sn-1 and sn-3 positions) and to breastfed milk, against allergy in term infants.

The three study groups are:

Group I—the InFat group, infants fed with the infant formula comprising InFat, enriched with palmitic acid at the sn-2 position;

Group II—the control group, infants fed with the vegetable oil mixture which comprises the same total amount of palmitic acid but mostly esterified to sn-1 and sn-3 positions;

Group III—the reference breastfeeding group, infants being breastfed.

The InFat infant formula (of Group I) and the control infant formula (of Group II) are essentially similar with respect to nutrient content and differ only in the position of palmitic acid in the triglyceride.

Immune Health Evaluation

Immune health consists of few elements:
1. incidence of allergy or atopy
2. incidence of infectious episodes Data is collected through follow-up visits, diaries written by parents, and telephone calls by trained personal.

In general, any sign or symptom related to allergy (Atopic dermatitis, wheezing episodes, and allergic urticaria) and infection (fever, cough, runny nose, and watery stools) is recorded, as well as any medical document.

During the study, parents are instructed to record allergic and infectious symptoms, every episode of fever, clinic visits, tests, physician's diagnosis, prescription of medications, particularly antibiotics, etc.

Additionally, each infant is monitored for anthropometric parameters, general health and well being.

Example 8

The Effect of Infant Formula with Different Fat Components on Intestinal Flora and Crying in Formula-Fed Chinese Infants Study Design The effect of the fat component in the infant formula on intestinal flora and crying is examined in a double blind randomized clinical trial in Chinese term formula fed infants with a reference arm of human breastfed infants.

Following screening, 114 healthy, growing, term infants are randomized to one of two treatment groups, 57 infants in the control group and 57 in the InFat group, with additional 57 breastfed infants as reference group.

Diets

The efficacy of infant formula with InFat™ is investigated in a double-blind, randomized, controlled 24 weeks duration trial in healthy term infants. The study is to demonstrate the effect of the infant formula with InFat™ compared to infant formula with standard vegetable oil (having high total palmitic mostly at sn-1 and sn-3 positions) and to breastfed milk, on intestinal microflora and crying in Chinese term infants.

The three study groups are:

Group I—the InFat group, infants fed with the infant formula comprising InFat, enriched with palmitic acid at the sn-2 position (20% total palmitic of which 44% is esterified to sn-2 position);

Group II—the control group, infants fed with the vegetable oil mixture which comprises the same total amount of palmitic acid but mostly esterified to sn-1 and sn-3 positions (20% total palmitic of which 13% is esterified to sn-2 position);

Group III—the reference breastfeeding group, infants being breastfed.

The InFat infant formula (of Group I) and the control infant formula (of Group II) are essentially similar with respect to nutrient content and differ only in the position of palmitic acid in the triglyceride. Both the formula of Group I and the formula of Group II include prebiotics. Therefore, the aim of the study is to show the effect of InFat on top of the effect of prebiotics.

Gut Flora Evaluation

Intestinal Flora:

Stool samples of at least 1 gr are collected from each infant in the study at baseline (inclusion to the study) and after 6 weeks. Samples are stored at 4° C. for up to 24 hrs before examination.

The tests performed on each sample include:

1. pH measurement to be determined based on pH level of a stool sample from the tested infant;

2. Specific bacterial counts on specific plates for a general estimation of different bacteria types such as:
 a. Lactobacilli on MRS+cys plate
 b. Bifidobacteria on MRS+++plate
 c. Coliforms on Mackonkey plate
 d. *E. coli* on TBX plate
 e. Enterobacteria on SB plate
 f. *Staphylococcus* on BP plate
 g. *Clostridium* on SPS plate
 h. *Pseudomonas* on pseudo-cent plate Further, parents are asked to fill 3 days diary of their infant feedings and significant crying periods.

Additionally, each infant is monitored for anthropometric parameters, general health and well being for safety assessment.

The invention claimed is:

1. A method of promoting development of beneficial gut flora in an infant consisting essentially of administering to said infant a lipid composition consisting essentially of an enzymatically prepared, vegetable-derived fat source consisting essentially of triglycerides,
 wherein said triglycerides consist essentially of fatty acid moieties with 15-55% of said fatty acid moieties being palmitic acid moieties; wherein at least 30% of said palmitic acid moieties are at the sn-2 position of the triglyceride backbone; wherein at least 50% of the total fatty acid moieties at the sn-1 and sn-3 positions of the triglyceride backbone are unsaturated; and wherein at least 35% of said unsaturated fatty acid moieties at the sn-1 and sn-3 positions are oleic acid moieties and at least 4% of said unsaturated fatty acid moieties at the sn-1 and sn-3 positions are linoleic acid moieties;
 wherein administration of the lipid composition has an effect on the immune system of the infant and the infant suffers from at least one disorder of the immune system resulting from gut flora imbalance, and is diagnosed with having an imbalance in the profile of the gut flora population compared to the gut flora profile of breastfed infants.
 so as to thereby promote development of beneficial gut flora in the infant.

2. The method of claim 1, wherein at least one pathogenic bacteria is present in the gut of the infant, wherein the lipid composition has an effect on colonization of said at least one pathogenic bacteria in the gut of the infant, and wherein the effect is selected from the group consisting of inhibiting, preventing and reducing colonization of the at least one pathogenic bacteria.

3. The method of claim 1, wherein said at least one disorder of the immune system is selected from the group consisting of inflammation, atopy, allergy, feeding intolerance and infection, and the lipid composition is effective to treat such disorder.

4. The method of claim 1, wherein the lipid composition promotes development of gut flora enhanced with bifidobacteria and lactobacilli.

5. The method of claim 2, wherein the lipid composition inhibits colonization of said at least one pathogenic bacteria in the gut of the infant.

6. The method of claim 1, wherein said infant was delivered by a Caesarean Section.

7. The method according to claim 1, wherein said infant is a newborn selected from pre-term infant and term infant.

8. The method of claim 1, wherein in said vegetable-derived fat source at least 13% w/w of the total fatty acid moieties at the sn-2 position of the triglyceride backbone are palmitic acid moieties.

9. The method of claim 1, wherein said vegetable-derived fat source comprises a fat base blended with a mixture of vegetable oils, wherein said mixture comprises oils selected from the group consisting of soy, palm tree, canola, coconut, palm kernel, sunflower, corn, safflower and rapeseed oil.

10. The method of claim 9, wherein said vegetable oils may be randomized before blending with the fat base.

11. The method of claim 1, wherein said vegetable-derived fat source is comprised in any one of food article and infant formula, wherein said food article is selected from bakery products, including bread, particularly biscuits and pastries, human milk fat substitute, dairy products, including milk and dairy drinks, ice cream, cereal products, sauces, soup, spreads, including margarine, fillings, oils and fats, soy products, meat products, fried food products, confectionery products, bars, candy bars, candies and chocolates, snacks, drinks and shakes, instant products, instant drink products, frozen food, prepared foods for infants, toddlers and young children, including prepared cooked mashed vegetables and/or fruits, condiment products, and cooking oils and fats.

12. The method of claim 11, wherein said infant formula comprises said vegetable-derived fat source, together with a protein source, a carbohydrate source, minerals, vitamins and optionally at least one of carrier, diluent, additive or excipient.

13. The method of claim 1, wherein the at least one disorder in the immune system is selected from asthma, eczema, rhinitis, and atopic dermatitis and the lipid composition is effective to treat the disorder.

* * * * *